(12) United States Patent
Yudoh

(10) Patent No.: US 8,440,893 B2
(45) Date of Patent: *May 14, 2013

(54) THERAPEUTIC AGENT FOR RHEUMATOID ARTHRITIS

(75) Inventor: Kazuo Yudoh, Yokohama (JP)

(73) Assignees: St. Marianna University School of Medicine, Kanagawa (JP); Mitsubishi Corporaion, Kanagawa (JP)

( * ) Notice: Subject to any disclaimer, the term of this patent is extended or adjusted under 35 U.S.C. 154(b) by 242 days.

This patent is subject to a terminal disclaimer.

(21) Appl. No.: 12/445,858

(22) PCT Filed: Oct. 18, 2007

(86) PCT No.: PCT/JP2007/070382
§ 371 (c)(1),
(2), (4) Date: Aug. 10, 2009

(87) PCT Pub. No.: WO2008/047880
PCT Pub. Date: Apr. 24, 2008

(65) Prior Publication Data
US 2010/0040599 A1   Feb. 18, 2010

(30) Foreign Application Priority Data
Oct. 20, 2006 (JP) .................. 2006-286774

(51) Int. Cl.
*A61K 9/14* (2006.01)
(52) U.S. Cl.
USPC ........... 977/915; 424/489; 514/825; 977/734; 977/735; 977/737; 977/738; 977/904
(58) Field of Classification Search ........................ None
See application file for complete search history.

(56) References Cited

U.S. PATENT DOCUMENTS

| 2002/0098180 A1 | 7/2002 | Lei et al. |
| 2004/0038946 A1* | 2/2004 | Wilson et al. .................. 514/102 |

(Continued)

FOREIGN PATENT DOCUMENTS

| EP | 1 867 337 A1 | 12/2007 |
| JP | 2006-160664 A | 6/2006 |

(Continued)

OTHER PUBLICATIONS

Ankylosing spondylitis [online] retrieved from: http://www.webmd.com/back-pain/guide/ankylosing-spondylitis?print=true# on Sep. 8, 2011; 3 pages.*

(Continued)

*Primary Examiner* — Ernst Arnold
(74) *Attorney, Agent, or Firm* — Kilpatrick Townsend & Stockton LLP

(57) ABSTRACT

When C60 was added to synovial fibroblasts, infiltrating lymphocytes, and macrophages, and the inflammatory cytokine production level was measured, the inflammatory cytokine production level was significantly suppressed in all cells. Furthermore, when C60 was added to osteoclast precursor cells and cultured in the presence of osteoclast differentiation-inducing factors, a certain concentration or more of C60 suppressed their differentiation into osteoclasts. Observation of the effect of C60 addition on bone resorption showed that C60 suppressed bone resorption by osteoclasts. In addition, the use of arthritis model animals confirmed in vivo that C60 suppressed inflammatory symptoms, as well as bone resorption and bone destruction by osteoclasts. C60 is effective for treating arthritic diseases such as rheumatoid arthritis through its effects of suppressing osteoclast differentiation, bone resorption, and inflammatory cytokines.

6 Claims, 16 Drawing Sheets

U.S. PATENT DOCUMENTS

2005/0221995 A1* 10/2005 Lowe .................... 508/113
2005/0239717 A1 10/2005 Kronholm et al.
2006/0134095 A1* 6/2006 Ito et al. ................. 424/125
2008/0107618 A1* 5/2008 Kepley .................. 424/78.27
2009/0104280 A1 4/2009 Yudoh

FOREIGN PATENT DOCUMENTS

WO   WO 01/80898 A1   11/2001
WO   WO 2006/101163 A1   9/2006

OTHER PUBLICATIONS

Sjogren syndrome [online] retrieved from: http://www.nlm.nih.gov/medlineplus/ency/article/000456.htm Jun. 28, 2011; 3 pages.*

Caplan's syndrome [online] retrieved from: http://www.nlm.nih.gov/medlineplus/ency/article/000137.htm; Jun. 10, 2011; 3 pages.*

Felty syndrome [online] retrieved from: http://www.nlm.nih.gov/medlineplus/ency/article/000445.htm; Jun. 28, 2011; 2 pages.*

Behcet's syndrome [online] retrieved from: http://www.nlm.nih.gov/medlineplus/behcetssyndrome.html; down loaded on Sep. 9, 2011; 2 pages.*

Polymyositis [online] retrieved from: http://www.mayoclinic.com/print/polymyositis/DS00334/DSECTION=all&METHOD=print; Jul. 7, 2011; 8 pages.*

Overlap syndrome [online] retrieved from: http://www.lupus.org/webmodules/webarticlesnet/templates/new_aboutindividualized.aspx?articleid=111&zoneid=18; downloaded on Sep. 9, 2011; 1 page.*

Autoimmune diseases [online] retrieved from: http://www.nlm.nih.gov/medlineplus/autoimmunediseases.html; downloaded on Sep. 9, 2011; 5 pages.*

Wermuth, Drug Discovery today 2006, 11(7/8), pp. 348-354.*

Osteoarthritis mayocllinic [online] retrieved from: http://www.mayoclinic.com/health/osteoarthritis/DS00019/METHOD=print; Nov. 24, 2010; 8 pages.*

Ankylosing spondylitis mayoclinic [online] retrieved from: http://www.mayoclinic.com/health/ankylosing-spondylitis/DS00483/METHOD=print; Feb. 3, 2011; 6 pages.*

Bonizzi, G., et al., "Reactive Oxygen Intermediate-Dependent NF-κb Activation by Interleukin-1β Requires 5-Lipoxygenase of NADPH Oxidase Activity," *Molecular and Cellular Biology*, vol. 19(3), pp. 1950-1960 (Mar. 1999).

Dröge, W., et al., "Free Radicals in the Physiological Control of Cell Function," *Physiol. Rev.*, vol. 82(1), pp. 47-95 (Jan. 2002).

Ha, H., et al., "Reactive oxygen species mediate RANK signaling in osteoclasts," *Experimental Cell Research*, vol. 301(2), pp. 119-127 (Dec. 10, 2004).

Henrotin, Y., et al., "Oxygen and reactive oxygen species in cartilage degradation: friends or foes?" *OsteoArthritis and Cartilage*, vol. 13(8), pp. 643-654 (Aug. 2005).

Ito, K., et al., "Reactive oxygen species act through p38 MAPK to limit the lifespan of hematopoietic stem cells," *Nature Medicine*, vol. 12(4), pp. 446-451 (Apr. 2006, Epub Mar. 26, 2006).

Lean, J., et al., "Hydrogen Peroxide Is Essential for Estrogen-Deficiency Bone Loss and Osteoclast Formation," *Endocrinology*, vol. 146(2), pp. 728-735 (Feb. 2005, Epub Nov. 4, 2004).

Lee, N., et al., "A crucial role for reactive oxygen species in RANKL-induced osteoclast differentiation," *Blood*, vol. 106(3), pp. 852-859 (Aug. 1, 2005, Epub Apr. 7, 2005).

Li, C., et al., "Manganese (III) acetate-mediated free radical reactions of [60]fullerene with β-dicarbonyl compounds," *Org. Biomol. Chem.*, vol. 2(23), pp. 3464-3469 (Dec. 7, 2004, Epub Oct. 20, 2004)

Mirkov, S., et al., "Nitric oxide-scavenging activity of polyhydroxylated fullerenol, $C_{60}(OH)_{24}$," *Nitric Oxide*, vol. 11(2), pp. 201-207 (Sep. 2004).

Raisz, L., et al., "Pathogenesis of osteoporosis: concepts, conflicts, and prospects," *The Journal of Clinical Investigation*, vol. 115(12), pp. 3318-3325 (Dec. 2005).

Trebble, T.M., "Bone turnover and nutritional status in Crohn's disease: relationship to circulating mononuclear cell function and response to fish oil and antioxidants," *Proceedings of the Nutrition Society*, vol. 64(2), pp. 183-191 (May 2005).

Williams, M., et al., "T Cell Receptor Stimulation, Reactive Oxygen Species, and Cell Signaling," *Free Radical Biology & Medicine*, vol. 37(8), pp. 1144-1151 (Oct. 15, 2004).

Yip, K., et al., "Thapsigargin Modulates osteoclastogenesis Through the Regulation of RANKL-Induced Signaling Pathways and Reactive Oxygen Species Production," *Journal of Bone and Mineral Research*, vol. 20(8), pp. 1462-1471 (Aug. 2005, Epub Mar. 28, 2005).

Yudoh, K., et al., "Water-Soluble C60 Fullerene Prevents Degeneration of Articular Cartilage in Osteoarthritis Via Down-Regulation of Chondrocyte Catabolic Activity and Inhibition of Cartilage Degeneration During Disease Development," *Arthritis & Rheumatism*, vol. 56(10), pp. 3307-3318 (Oct. 2007).

* cited by examiner

THERAPEUTIC AGENT FOR RHEUMATOID ARTHRITIS

CROSS-REFERENCE TO RELATED APPLICATIONS

This application is a U.S. National Phase of PCT/JP2007/070382, filed Oct. 18, 2007, which claims the benefit of Japanese Application No. 2006-286774, filed Oct. 20, 2006, the contents of which are herein incorporated by reference.

TECHNICAL FIELD

The present invention relates to novel uses of fullerenes, and particularly relates to novel therapeutic agents for rheumatoid arthritis comprising a fullerene as an active ingredient.

BACKGROUND ART

Rheumatoid arthritis is a chronic inflammatory disease in which the synovial membrane is the primary site of inflammation. Bone destruction occurs with the progression of inflammation, resulting in deformation or damage of bones and cartilages. Rheumatoid arthritis sometimes develops into a wasting disease accompanying not only inflammation of synovial membranes or osteoarticular tissues, but also systemic inflammation, causing disorders in various organs and tissues, and may even lead to severe symptoms affecting life prognosis.

Rheumatoid arthritis is considered to develop as a result of the complex involvement of many factors, and the mechanism of its onset has not been fully elucidated. However, clinical observations have shown villous hyperplasia of synovial membranes with angiogenesis, and infiltration of inflammatory cells (lymphocytes and macrophages) that produce various inflammatory cytokines or growth factors, into synovial tissues. Accordingly, the various arthritic symptoms of rheumatoid arthritis are thought to arise due to the close involvement of infiltrating inflammatory cell activation in synovial membranes. Furthermore, bone and articular tissues of rheumatoid arthritis patients show villous-like proliferated synovial membranes invading and destroying articular tissues, mainly bone tissues. Thus, villous proliferation of the synovial membrane is considered to be a direct cause of inflammation-associated paraarticular osteoporosis and damage to articular function (support, mobility, and indolence).

In Japan, the number of patients with arthritis, in particular rheumatoid arthritis, is said to have reached over 700,000. Since rheumatoid arthritis develops in people in their thirties and forties and gradually becomes advanced and aggravated during the middle to old age, it significantly affects daily life. Therefore, vigorous research and development of anti-rheumatic agents have been carried out in and outside of Japan. In recent years, anti-cytokine therapies targeting inflammatory cytokines have been receiving attention, and novel biopharmaceuticals having effective anti-rheumatic actions, such as infliximab, etanercept, anakinra, and atlizumab, have been developed.

However, even superior anti-rheumatic agents are not effective for all patients, and there are always responders and non-responders to each type of anti-rheumatic agent. Moreover, due to long-term administration of a pharmaceutical agent, even responders often show a resistance effect (reduced drug efficacy), thereby requiring increased dosage of the agent or a switch to another agent. Furthermore, complications or past illnesses of a patient may often limit the administration of anti-rheumatic agents. To rescue patients non-responsive to conventional anti-rheumatic agents and those cases that do not allow the administration of anti-rheumatic agents due to complications, development of novel anti-rheumatic agents is still very much in need.

As rheumatoid arthritis progresses, bone destruction takes place. Bone destruction is mediated by osteoclasts. Osteoclasts differentiate from bone marrow monocyte/macrophage lineage precursor cells, and the RANKL (receptor activator of NF-κB ligand)-RANK signal is known to be deeply involved in inducing the differentiation. RANKL was initially reported as a dendritic cell activator, but was later found to be identical to osteoclast differentiation factor (ODF) expressed in osteoclastogenesis-supporting cells. RANKL is a type II transmembrane protein belonging to the TNF ligand family, but it is also produced as the soluble type by cleavage of the membrane type by a metalloprotease. Both the membrane-type RANKL and the soluble-type RANKL exist as homotrimers, and act as agonists against RANK (receptor activator of NF-κB). RANKL is induced by IL-1, IL-6, TNF-α, and such, and is expressed in osteoblasts, synovial fibroblasts, activated T-cells, etc. RANK, a receptor of RANKL, is a type I membrane protein expressed in dendritic cells, osteoclast precursor cells, and such, and has binding sites for Traf1, 2, 3, 5, and 6 in its intracellular domain. When RANKL binds to RANK on an osteoclast precursor cell, the RANKL-RANK signal is transmitted downstream to Traf 6, NF-κB, JNK, p38, and such, and osteoclast differentiation is induced. Recently, it has been successively reported that reactive oxygen species (ROS) play an important role in RANKL signal-mediated osteoclast differentiation (Non-Patent Documents 1-4).

While the etiology of rheumatoid arthritis is closely associated with inflammatory cytokines (TNF-α, IL-1, IL-6, and such) produced mainly by macrophages, reactive oxygen species are involved in activating lymphocytes that induce the activation of these macrophages (Non-Patent Document 5). Furthermore, it is known that intracellular production of reactive oxygen species increases with stimulation by TNF-α, IL-1, IL-6, or such, and that reactive oxygen species play an important role as messengers in the intracellular signal transduction pathway (NFkB, P38, and PI-3 kinase) (Non-Patent Documents 6-7).

On the other hand, excessively produced, high concentrations of reactive oxygen species induce cytotoxicity or cell death. This means that scavenging excessive reactive oxygen species leads to suppression of cell activity decrease, suppression of cell aging and death, and prolongation of the life span of cells. Thus, if the cell death or cell activity decrease of inflammatory cytokine-producing cells is suppressed by scavenging reactive oxygen, cell activities (induction of cytokine production, and differentiation and maturation of osteoclasts) will increase as a result, and consequently, this may lead to aggravation of rheumatic diseases. In fact, increase in intracellular reactive oxygen has been reported to cause cellular aging and decreased cell activity of hematopoietic stem cells through the cell signaling pathway mediated by p38 kinase (Non-Patent Document 8). This finding suggests the possibility that scavenging reactive oxygen species may lead to the suppression of aging and the activation of cells.

Accordingly, reactive oxygen is deeply involved in intracellular signal transduction, and may regulate life activities by having both positive and negative effects on cells. Which of the opposing effects of reactive oxygen become dominant may depend on the characteristics and environment of respective cells receiving those effects, and therefore cannot be definitely conceived.

Fullerene is known to have the ability to capture/scavenge free radicals (Non-Patent Documents 9-10).

Non-Patent Document 1: Ha H. et al. Exp Cell Res. 2004 Dec. 10; 301(2): 119-27
Non-Patent Document 2: Lee J M et al. Blood. 2005 Aug. 1; 106(3):852-9
Non-Patent Document 3: Lean J M et al. Endocrinology. 2005; 146:728-35
Non-Patent Document 4: Yip K H et al. J Bone Miner Res. 2005 20(8): 1462-71
Non-Patent Document 5: Williams M S and Kwon J. Free Radical Biology & Medicine. 2004; 1144-1151
Non-Patent Document 6: Bonizzi G et al. Mol. Cell. Biol. 1999 March; 19(3): 1950-60
Non-Patent Document 7: Droge W. Physiol. Rev. 2002 January; 82(1): 47-95
Non-Patent Document 8: Ito K et al. Nature medicine, 12(4), 446-451
Non-Patent Document 9: Li C, et al., Org Biomol Chem. 2004 Dec. 7; 2(23):3464-9.
Non-Patent Document 10: Mirkov S M, et al., Nitric Oxide. 2004 September; 11(2):201-7.

DISCLOSURE OF THE INVENTION

Problems to be Solved by the Invention

The present invention was made in view of the above circumstances. An objective to be achieved by the present invention is to provide novel pharmaceutical agents for treating and/or preventing arthritis-accompanying diseases, including rheumatoid arthritis.

Means for Solving the Problems

The present inventors made dedicated efforts to achieve the above-mentioned objective. They focused on the ability of fullerenes to capture/scavenge free radicals, and conceived using them as therapeutic agents for rheumatoid arthritis and such. As described above, effects of reactive oxygen species on a living organism are highly complicated, and reactive oxygen species may have double-edged effects on arthritis-accompanying diseases such as rheumatoid arthritis. Furthermore, there have been no reports on the use of fullerene for treating arthritis and such. Therefore, it was impossible to predict whether or not fullerene administration would be effective for rheumatoid arthritis. Nevertheless, the present inventors examined the possibility of treating rheumatoid arthritis using fullerenes. First, since arthritis is an inflammatory disease whose primary site is the intraarticular synovial membrane, direct action of C60 on synovial fibroblasts, infiltrating lymphocytes, and macrophages were examined. When C60 was added to synovial fibroblasts, infiltrating lymphocytes, and macrophages, and the production levels of inflammatory cytokines (TNF-α and IL-1β) in these cells were measured, the inflammatory cytokine production levels were significantly suppressed in all of these cells, and the inhibitory effect of C60 on inflammatory cytokine production was observed. Next, to investigate the possibility of using C60 to treat or prevent bone destruction, which is one of the main symptoms of rheumatoid arthritis, effects of C60 on the differentiation of osteoclasts and bone resorption by osteoclasts were examined. When C60 was added to osteoclast precursor cells and cultured in the presence of osteoclast differentiation-inducing factor, a certain level or more of C60 suppressed the differentiation into osteoclasts. Furthermore, the observation of the effects of C60 addition on bone resorption showed that C60 suppressed bone resorption by osteoclasts. While it had been expected from previous findings that fullerenes would have either aggravating or improving effects on bone destruction and inflammatory cytokine production, and therefore it was completely impossible to predict which effect would be actually exerted, the above examinations have directly and specifically proved that fullerenes have suppressing actions on osteoclast differentiation and bone resorption, and are useful for the prevention and treatment of bone destruction. Furthermore, comparison of C60 and other reactive oxygen scavengers for the antioxidative action, ability to suppress inflammatory cytokine production, and ability to suppress osteoclast differentiation revealed that fullerenes have a much stronger antioxidative action, inflammatory cytokine production-suppressing ability, and osteoclast differentiation-suppressing ability than other reactive oxygen scavengers. Therefore, if fullerenes are administered such that they can reach the joints, they may exhibit the inflammatory cytokine-suppressing action on synovial tissues (synovial fibroblasts and infiltrating lymphocytes), thereby resulting in outcomes effective for treating arthritic diseases including rheumatoid arthritis. Furthermore, since C60 has suppressing effects on osteoclast differentiation and bone resorption, fullerenes may also be effective for osteoporosis in which osteoclasts are involved. Thus, the present invention relates to novel pharmaceutical agents using fullerenes, and more specifically provides the following:

(1) a pharmaceutical agent for treating and/or preventing rheumatoid arthritis, an arthritis-accompanying rheumatoid arthritis-related disease, an arthritis-accompanying autoimmune disease, or osteoporosis, comprising at least one pharmaceutical agent selected from the group consisting of a fullerene, a clathrate fullerene, and a fullerene derivative;

(2) the pharmaceutical agent of (1), wherein the arthritis-accompanying rheumatoid arthritis-related disease or arthritis-accompanying autoimmune disease also accompanies bone destruction;

(3) a pharmaceutical agent for treating and/or preventing bone destruction in rheumatoid arthritis, arthritis-accompanying rheumatoid arthritis-related disease, arthritis-accompanying autoimmune disease, or osteoporosis, comprising a substance having an ability to scavenge reactive oxygen;

(4) a pharmaceutical agent for treating and/or preventing inflammation in rheumatoid arthritis, arthritis-accompanying rheumatoid arthritis-related disease, arthritis-accompanying autoimmune disease, or osteoporosis, comprising a substance having an ability to scavenge reactive oxygen;

(5) the pharmaceutical agent of any one of (1) to (4), wherein the substance having an ability to scavenge reactive oxygen is at least one selected from the group consisting of a fullerene, a clathrate fullerene, and a fullerene derivative;

(6) the pharmaceutical agent of any one of (1) to (5), wherein the arthritis-accompanying rheumatoid arthritis-related disease is at least one selected from the group consisting of malignant rheumatoid arthritis, Felty's syndrome, and Caplan's syndrome;

(7) the pharmaceutical agent of any one of (1) to (6), wherein the arthritis-accompanying autoimmune disease is at least one selected from the group consisting of systemic lupus erythematosus, polymyositis, psoriatic arthritis, Bechet's disease, Sjogren's syndrome, mixed connective tissue disease, and overlap syndrome;

(8) the pharmaceutical agent of any one of (1) to (7), wherein the fullerene is C60;

(9) the pharmaceutical agent of any one of (1) to (8), which is an injection;

(10) an osteoclast differentiation inhibitor comprising at least one selected from the group consisting of a fullerene, a clathrate fullerene, and a fullerene derivative;

(11) a bone resorption inhibitor comprising at least one selected from the group consisting of a fullerene, a clathrate fullerene, and a fullerene derivative;

(12) an inflammatory cytokine production inhibitor comprising at least one selected from the group consisting of a fullerene, a clathrate fullerene, and a fullerene derivative;

(13) the inflammatory cytokine production inhibitor of (12), wherein the inflammatory cytokine comprises at least one selected from the group consisting of TNF-α, IL-6, IL-1, and IL-17;

(14) a pharmaceutical agent for treating and/or preventing rheumatoid arthritis, arthritis-accompanying rheumatoid arthritis-related disease, arthritis-accompanying autoimmune disease, or osteoporosis, comprising any one of the osteoclast differentiation inhibitors of (10), bone resorption inhibitors of (11), and the inflammatory cytokine production inhibitors of (12);

(15) a method for treating and/or preventing a disease expressing arthritis, comprising the step of administering at least one selected from the group consisting of a fullerene, a clathrate fullerene, and a fullerene derivative;

(16) the method of (15), wherein the disease expressing arthritis is any one of rheumatoid arthritis, rheumatoid arthritis-related disease, autoimmune disease, and osteoporosis;

(17) a method of suppressing osteoclast differentiation, comprising the step of administering at least one selected from the group consisting of a fullerene, a clathrate fullerene, and a fullerene derivative;

(18) a method of suppressing bone resorption, comprising the step of administering at least one selected from the group consisting of a fullerene, a clathrate fullerene, and a fullerene derivative;

(19) a method of suppressing inflammatory cytokine production, comprising the step of administering at least one selected from the group consisting of a fullerene, a clathrate fullerene, and a fullerene derivative;

(20) use of a fullerene, a clathrate fullerene, and/or a fullerene derivative for producing a pharmaceutical agent for treating and/or preventing arthritis;

(21) use of a fullerene, a clathrate fullerene, and/or a fullerene derivative for producing an osteoclast differentiation inhibitor;

(22) use of a fullerene, a clathrate fullerene, and/or a fullerene derivative for producing a bone resorption inhibitor; and

(23) use of a fullerene, a clathrate fullerene, and/or a fullerene derivative for producing an inflammatory cytokine production inhibitor.

BEST MODE FOR CARRYING OUT THE INVENTION

Figure 1:
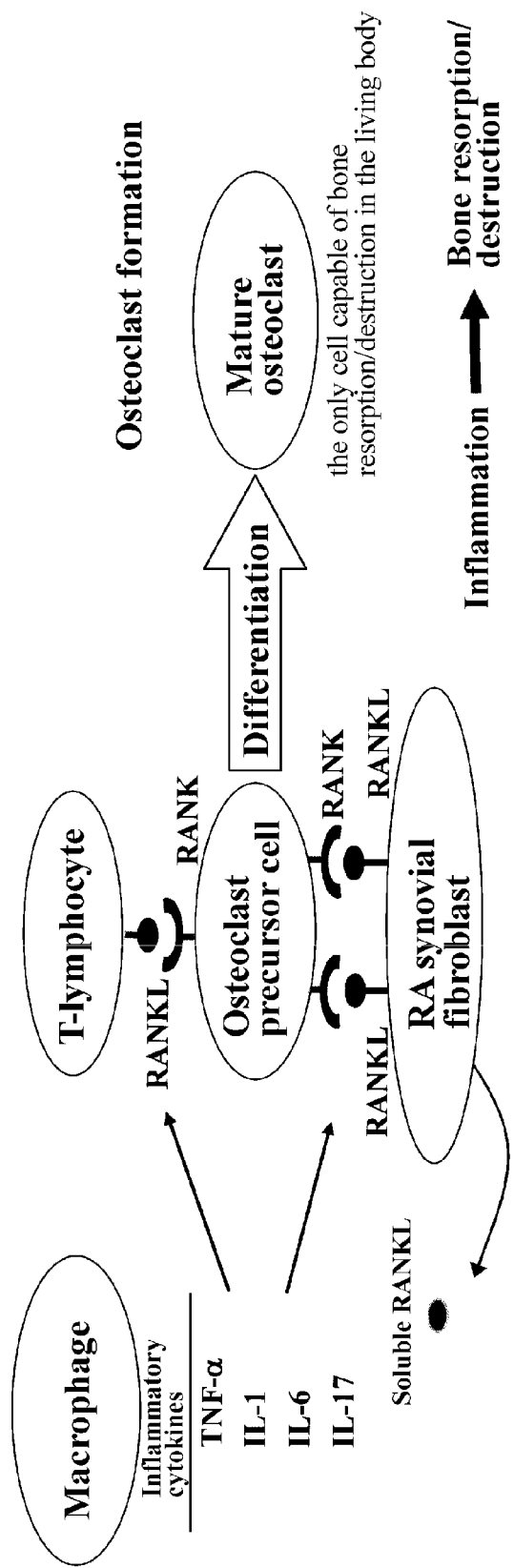
FIG. 1: depicts the relationship between osteoclasts and factors involved in osteoclast maturation.

As the first embodiment, the present invention provides pharmaceutical agents for treating and/or preventing rheumatoid arthritis, an arthritis-accompanying rheumatoid arthritis-related disease, arthritis-accompanying autoimmune disease, or osteoporosis, which use a fullerene, a clathrate fullerene, a fullerene derivative, or a salt thereof (hereinafter, also referred to as "fullerenes"). The present inventors confirmed that inflammatory cytokine production in cells associated with arthritis is suppressed by fullerene administration. Furthermore, the present inventors confirmed that fullerenes suppress differentiation of precursor cells to osteoclasts, and also bone resorption by osteoclasts. In addition, the present inventors confirmed in vivo using arthritis model animals that fullerenes actually suppress inflammation and bone resorption/destruction in arthritis. Therefore, fullerenes can be used as therapeutic and preventive agents for diseases accompanying inflammation and bone destruction.

Fullerene is typically a molecule having a closed pseudo-spherical structure in which each of the 20 or more carbon atoms is bound to the adjacent three atoms. The known numbers of carbon atoms are 60, 70, 76, 78, and the like. In the present invention, any one of these fullerenes such as C60 and C70 can be suitably used, as long as it has an activity capable of scavenging reactive oxygen. Moreover, fullerene derivatives such as heterofullerene, norfullerene, homofullerene, secofullerene, chemically modified fullerenes, fullerene polymers, and salts thereof can also be suitably used, as long as they have the abovementioned activity or effect. Chemical modifications include hydrogenation and addition of substituents to fullerene. Examples of substituents that can be added to fullerene include hydroxyl groups, but are not specifically limited thereto as long as the reactive oxygen scavenging ability of fullerene can be retained and cytotoxicity can be kept low. Moreover, the proportion of the additional substituents to carbons can be appropriately adjusted considering the reactive oxygen scavenging ability and influence on cytotoxicity. Besides modification using substituents, modification using hydrophilic high molecules and the like may be performed to improve fullerene compatibility with cells and tissues. Examples of such hydrophilic high molecules include polyethylene glycol, hyaluronic acid, and the like.

Fullerene is normally hydrophobic, and is poorly soluble in water. Therefore, fullerene may be made hydrophilic (water-solubilized) and used for the sake of formulation convenience or the like, when fullerene is used as an agent of the present invention. Examples of means for water-solubilizing fullerene include the addition of hydrophilic substituents such as a hydroxyl group, an amino group, and a carboxyl group. Hydroxylated fullerenes are examples of hydrophilic fullerenes that can be suitably used. Specific examples of commercially available hydroxylated fullerenes include "Nanom Spectra" manufactured by Frontier Carbon Corporation.

Moreover, other means for water-solubilizing fullerene include clathration with water-soluble high molecules (such as polyvinyl pyrrolidone (PVP)) or water-soluble macrocyclic compounds (such as cyclodextrin). Such clathrated fullerenes (clathrate fullerenes) are one of the "fullerenes" that are suitably used as an agent of the present invention.

The cytotoxicity of fullerenes can be assessed by, for example, the XTT method using water-soluble tetrazolium salts. Moreover, the reactive oxygen scavenging ability of fullerenes with modifications and the like, may be measured by methods for measuring the antioxidative ability of the fullerenes, an example of which includes the method using copper ion-reducing power as an index (Schitt AA, Pergamon Press, London, Newwork, Paris, 1966, Yamashita N et al., Alpha-tocopherol induces oxidative damage to DNA in the presence of copper (II) ions. Chemical Res. Toxicl. 11:855-862, 1998), or the like. Specifically, evaluation can be performed by contacting $Cu^{2+}$ ions and a fullerene, and using as an index, whether the reduction reaction from $Cu^{2+}$ into $Cu^+$ can be inhibited (copper ion-reducing power). In addition, the reactive oxygen scavenging ability of fullerenes may be measured by antioxidative ability evaluation methods which utilize weak luminescence emitting when reactive oxygen (hydrogen peroxide) reacts with an antioxidant (Y) (weak luminescence spectrometry for analyzing reactive oxygen scavenging), analytical methods for superoxide scavenging activity (SOD-like activity), or the like.

Fullerenes of the present invention are effective for diseases expressing arthritis or bone destruction. A representative example of such diseases expressing arthritis or bone destruction is "rheumatoid arthritis". The Japan College of Rheumatology refers to "chronic rheumatoid arthritis" by the unified name "rheumatoid arthritis". Therefore, chronic rheumatoid arthritis is included in the "rheumatoid arthritis" in the present invention. Several diseases related to rheumatoid arthritis are also known. For example, malignant rheumatoid arthritis expresses vasculitis and serious multiple organ symptoms in addition to arthritis. Felty's syndrome expresses a swollen spleen or leukopenia in addition to arthritis. Caplan's syndrome accompanies pneumoconiosis in addition to arthritis. Since fullerenes of the present invention have been confirmed to suppress inflammatory cytokine production from cells involved in arthritis as described above, these "rheumatoid arthritis-related diseases" can also be treated or prevented effectively by the fullerenes of the present invention in that these diseases are associated with arthritis. Furthermore, some autoimmune diseases are known to accompany arthritis, and such autoimmune diseases accompanying arthritis are also expected to be treated or prevented using fullerenes of the present invention. Specific examples of "autoimmune diseases accompanying arthritis" expected to be treated or prevented by fullerenes of the present invention include systemic lupus erythematosus, polymyositis, psoriatic arthritis, Bechet's disease, Sjogren's syndrome, mixed connective tissue disease, and overlap syndrome. However, the autoimmune diseases to which fullerenes of the present invention are applicable are not limited thereto, and any autoimmune disease may be treated with fullerenes of the present invention as long as it accompanies arthritis.

Since the fullerenes of the present invention have been confirmed to suppress the differentiation of osteoclasts and bone resorption by osteoclasts both in vitro and in vivo, they may effectively treat or prevent any diseases accompanying bone destruction. Examples of diseases accompanying bone destruction include, in addition to rheumatoid arthritis, bone destruction-accompanying rheumatoid arthritis-related diseases, bone destruction-accompanying autoimmune diseases, and osteoporosis. Malignant rheumatoid arthritis, Felty's syndrome, and Caplan's syndrome are examples of rheumatoid arthritis-related diseases with bone destruction. Furthermore, systemic lupus erythematosus, polymyositis, psoriatic arthritis, Bechet's disease, Sjogren's syndrome, mixed connective tissue disease, and overlap syndrome are known to accompany bone destruction. Osteoporosis is roughly classified into either primary osteoporosis, which is caused by menopause or aging, or secondary osteoporosis, which occurs following a primary disorder such as hyperparathyroidism, renal diseases, liver diseases, gastrointestinal diseases, diabetes, artificial menopause due to ovariectomy, long term administration of large doses of steroids, chronic inflammatory diseases including rheumatoid arthritis, osteomalacia, or osteogenesis imperfecta. In each case, the bone mass decreases as osteoclastic bone resorption becomes dominant over bone production. Since the fullerenes of the present invention have an effect of suppressing osteoclastic bone resorption, they may be effective for any type of osteoporosis regardless of whether it is primary or secondary, and regardless of the primary disorder in the case of secondary osteoporosis.

Rheumatoid arthritis patients often show systemic steroidal osteoporosis, disuse osteoporosis due to pain, and local juxta-articular osteoporosis. Juxta-articular osteoporosis is an osteoporosis that develops around rheumatoid arthritis-affected joints. The cause of juxta-articular osteoporosis is thought to be enhanced activation of osteoclasts in and around the joints. Inflammatory cytokines relating to arthritis, and osteoclast differentiation that is activated and enhanced by such inflammatory cytokines are considered to trigger osteoporosis around the joints. The fullerenes of the present invention are expected to have dual effects on juxta-articular osteoporosis: direct suppression of osteoclast differentiation (effect of removing ROS, a RANK-RANKL signal messenger, and thereby inhibiting the RANK-RANKL signal to suppress the osteoclast differentiation) and secondary suppression of osteoclast differentiation caused by the inflammation-suppressing effect (effect of suppressing inflammatory cytokine production and thereby suppressing the inflammatory cytokine-induced enhancement of the RANK-RANKL signal to secondarily suppress the osteoclast differentiation). Therefore, the fullerenes of the present invention may be particularly effective for juxta-articular osteoporosis which follows rheumatoid arthritis.

As the second embodiment, the present invention provides a pharmaceutical agent for treating and/or preventing bone destruction in rheumatoid arthritis, arthritis-accompanying rheumatoid arthritis-related diseases, arthritis-accompanying autoimmune diseases, or osteoporosis, wherein the agents comprise a substance having the ability to scavenge reactive oxygen. The present inventors confirmed that fullerene significantly suppresses osteoclast differentiation. This effect of fullerene in suppressing osteoclast differentiation may be a result of capturing ROS, a RANKL-RANK signal mediator, which downregulates the RANKL-RANK signal when osteoclast precursor cells differentiate into osteoclasts. Therefore, similar to fullerenes, substances capable of scavenging reactive oxygen may effectively suppress bone destruction in which the RANKL-RANK signal is involved. The bone destruction that can be treated or prevented by fullerenes of the present invention is not particularly limited so long as it involves the RANKL-RANK signal, and examples include bone destruction in rheumatoid arthritis, an arthritis-accompanying rheumatoid arthritis-related disease, an arthritis-accompanying autoimmune disease, or osteoporosis.

There is no particular limitation on the type of substances capable of scavenging reactive oxygen in the present invention so long as they have the ability to scavenge reactive oxygen. In general, examples of substances capable of scavenging reactive oxygen include fullerenes, vitamin E, vitamin A, carotene, superoxide dismutase (SOD), catalase, polyphenols, and glutathione peroxidase. The ability of a substance to scavenge reactive oxygen can be determined by the above-mentioned method using the copper ion-reducing power as an index. The substances capable of scavenging reactive oxygen of the present invention are preferably fullerenes.

Since the present inventors confirmed that fullerenes suppress the production level of TNF-α and IL-1β, the fullerenes of the present invention can be used as inhibitors of inflammatory cytokine production. Generally, the term "inflammatory cytokines" collectively refers to cytokines involved in eliciting an inflammatory response in vivo, and typical inflammatory cytokines include TNF-α, IL-1, and IL-6. Whether or not fullerenes have an ability to suppress inflammatory cytokine production can be determined by culturing cells in the presence of fullerenes, and measuring the production level of inflammatory cytokines by known methods such as the ELISA method. As shown in the Examples, fullerenes that suppress inflammatory cytokine production in cells associated with arthritis are effective for treating and preventing various types of arthritis including rheumatism through suppression of the production level of inflammatory cytokines. Furthermore, TNF-α, IL-1, and IL-6 are called bone-resorbing cytokines and are known to promote bone resorption. Therefore, fullerenes that suppress the production of these bone-resorbing cytokines are useful for treating and preventing bone destruction.

As described above, fullerenes may be used to produce pharmaceuticals for rheumatoid arthritis, arthritis-accompanying rheumatoid arthritis-related diseases, arthritis-accompanying autoimmune diseases, or osteoporosis. When the above pharmaceuticals are prepared, the fullerene may be appropriately mixed with suitable additives and formulated via various processes. The additives used for preparing formulations may be selected from pharmaceutically acceptable additives according to the purposes. "Pharmaceutically acceptable additives" include excipients, diluents, extenders, disintegrators, stabilizers, preservatives, buffering agents, emulsifiers, aromatic substances, colorants, sweeteners, thickening agents, flavoring agents, solubilizing agents, and other additives. A fullerene can be formed into a pharmaceutical composition for treating motor organ diseases by mixing directly with various additives, or by mixing with them after dissolving the fullerene in an appropriate solvent, and subjecting to various processes such as granulation, sorting, kneading, shaping, drying, tablet-making, packing, sterilization, and aseptic filtration, according to the desired form of formulation. Formulation of pharmaceutical compositions according to the present invention may be in any form such as oral agents (tablets, granules, solutions, capsules, and the like), injections, patches, liniments, suspensions, emulsions, or ointments, as long as the form allows the composition to reach an affected part. However, injections and the like which can be directly injected into an affected part are preferable as a method that reliably delivers an agent to an affected part. Injections, for example, can be produced by dissolving, suspending, or emulsifying fullerene in a pharmaceutically acceptable carrier to meet the dosage described below. As a carrier used for injections, non-aqueous diluents (such as propylene glycol, polyethylene glycol, vegetable oil such as olive oil, and alcohols such as ethanol) may be adopted as well as physiological salt solutions or commercially available distilled water for injection. The injections can be sterilized by filter sterilization using a bacteria-retaining filter, by mixing disinfectants, or by irradiation. The injections can be produced in a form that allows preparation when needed. That is, sterile fullerenes prepared by lyophilization and the like, can be used by dissolving in a sterile carrier before use.

Moreover, dosage of pharmaceutical compositions of the present invention can be appropriately determined according to the condition, size and the like of the affected part; the dosage can be 0.1 µM to 1000 µM, preferably 10 µM to 200 µM, and more preferably 10 µM to 100 µM per affected part. Since the dosage varies according to various conditions, amounts smaller than the above dosage may be sufficient in some cases, and dosages over the above range may be required in others.

The pharmaceutical agents of the present invention may be administered in combination with another pharmaceutical agent. For example, when a pharmaceutical agent of the present invention is used to treat rheumatoid arthritis and related diseases, it may be combined with a disease-modifying anti-rheumatic drug (DMARD). Examples of disease-modifying anti-rheumatic drugs include immunomodulatory agents (gold sodium thiomalate, auranofin, penicillamine, salazosulfapyridine, bucillamine, lobenzarit, actarit, etc.), immunosuppressive agents (methotrexate, leflunomide, mizoribine, azathioprine, cyclophosphamide, cyclosporine, tacrolimus, etc.), chimeric TNFα monoclonal antibody (infliximab), soluble TNF receptor fusion protein (etanercept), human anti-TNFα monoclonal antibody (adalimumab), IL-1 receptor antagonist, and humanized anti-IL-6 receptor antibody (MRA); however, the pharmaceutical agents that can be used in combination with the pharmaceutical agents of the present invention are not limited thereto. Furthermore, in addition to the above-mentioned combined uses, a pharmaceutical agent applied to rheumatic diseases such as a non-steroidal anti-inflammatory drug (NSAID) may also be administered in combination. When the pharmaceutical agents of the present invention are used in combination with other pharmaceutical agents, they may be individually prepared as separate formulations. Alternatively, the fullerenes of the present invention and other pharmaceutical agents may be formulated in a single combination agent. For example, a combination agent containing a fullerene of the present invention and DMARD may be prepared. Alternatively, a single kit containing a fullerene of the present invention and DMARD may be prepared.

All prior art references cited in this specification are incorporated herein by reference.

EXAMPLES

Herein below, the present invention will be specifically described with reference to Examples, but it is not to be construed as being limited thereto.

Example 1

Effects of C60 on the Activation of Inflammatory Cells (Synovial Fibroblasts, Infiltrating Lymphocytes and Macrophages)

Since arthritis is an inflammatory disease whose primary site is intraarticular synovial membrane, direct actions of C60 on synovial fibroblasts and infiltrating lymphocytes were examined. In particular, effects of C60 addition on inflammatory cytokine production from the above-mentioned cells were examined.

Example 1-1

Cell Culture

Synovial fibroblasts isolated from human articular synovial tissues, and lymphocytes and macrophages separated from the blood of healthy individuals were used for culture.

i) Preparation of Synovial Fibroblasts

After obtaining informed consent, synovial tissues were collected from surgically-removed tissues from rheumatoid arthritis patients. The synovial tissues were sliced and then treated in a liquid low-glucose Dulbecco's modified Eagle's medium (DMEM, manufactured by Gibco Co.) containing 1.0 mg/ml collagenase at 37° C. overnight, to isolate synovial fibroblasts for culture. The cells were normally cultured in a culture flask (culture area: 25 cm$^2$), and in a polystyrene culture dish (diameter: 6 cm) when used in experiments. The cell culture was performed using a DMEM medium added with inactivated fetal bovine serum (FBS, manufactured by TRACE Co.) at 10% volume of the medium, and also 2 mM L-glutamine, 25 mM HEPES, and penicillin and streptomycin at 100 units/ml, in a $CO_2$ incubator which was set at 5% $CO_2$+95% air (normoxic conditions) at 37° C. under saturated humidity. For passaging, the cells were washed with a phosphate buffer solution (PBS, manufactured by Nissui Co.), peeled off using a 0.25% trypsin-PBS solution (Gibco Co.), dispersed by pipetting and diluted with the medium to an appropriate concentration.

ii) Preparation of Lymphocytes and Macrophages

After obtaining informed consent, 50 mL of blood was collected from healthy individuals, and 1% heparin-added blood was acquired. Centrifuge tubes in which this blood was layered on top of a lymphocyte separation liquid were centrifuged at 1500 rpm for 30 minutes to isolate lymphocytes and macrophages individually. The cells were cultured using an RPMI medium supplemented with inactivated fetal bovine serum (FBS, manufactured by TRACE) at 10% of the medium volume, and also with 2 mM L-glutamine, 25 mM HEPES, and 100 units/mL of penicillin and streptomycin, in a $CO_2$ incubator set at 5% $CO_2$+95% air (normoxic conditions) at 37° C. under saturated humidity.

Example 1-2

Cell Growth Ability

Effects of C60 on the viability of synovial fibroblasts, lymphocytes, and macrophages were evaluated by the XTT method.

C60 (crown-fullerene: manufactured by Frontier Carbon Corp.) was dissolved in PBS to prepare a 40 µM stock solution, and this was stored in a dark place at −20° C.

The C60 concentrations used for treatment were 0.1 µM, 1.0 µM, and 10.0 µM, and the drug treatment durations were 48 hours and 96 hours. 50 µL of each type of cell in the logarithmic growth phase was added to a 96-well microplate at a concentration of 5.0×10$^5$ cells/mL, and cultured for 24 hours in a $CO_2$ incubator (normoxic condition). C60 was added at each of the desired concentrations (final volume of 100 µL) to the 96-well microplate. After culturing for 48 or 96 hours, the medium was exchanged, and the cells were further cultured for 12 hours. 50 µL of the XTT reagent was added to each well, and cultured for four hours. Then, the absorbance at 450 nm was immediately measured using a plate reader to analyze the cell viability.

The results of the above examination showed that the addition of 0.1, 1.0, or 10.0 µM C60 has no effect on the cell viability of any of the synovial fibroblasts, lymphocytes, and macrophage cells (n=5 for each type of cell).

Example 1-3

Effects of C60 on the Ability to Produce Inflammatory Cytokines

Effects of C60 on the production of inflammatory cytokines in each type of cell were analyzed using the enzyme-linked immunosorbent assay method (ELISA).

Each type of cell that was isolated and cultured to subconfluency by the above method was seeded into a 24-well culture plate at $1\times10^5$ cells/well. After culturing for 12 hours, the cells were washed with PBS, the medium was exchanged to fresh DMEM containing 10% FBS, and tumor necrosis factor TNF-α was added. The concentration of C60 treatment was 0.1, 1.0, or 10.0 μM, and the concentration of TNF-α treatment was 10.0 ng/mL. Each type of cell was cultured with C60 for 24 hours in the presence or absence of TNF-α, and then the culture solution was collected.

The concentrations of inflammatory cytokines TNF-α and interleukin (IL)-1β in the culture supernatant were determined using a ELISA kit, which is a standard technique currently known in the art. The ELISA was performed by the following standard method: the diluted culture supernatant sample was added into a sensitized plate at 100 μl per well, and the plate was left still for one hour at room temperature (primary reaction). After the primary reaction, the wells were sufficiently washed with PBS using a wash bottle four times or more. Horseradish peroxidase (HRP)-labeled goat anti-rabbit IgG (H+L) antibodies that have been diluted 3,000-folds with 0.1% Tween20-PBS were dispensed into the respective wells at 100 μl each, and the plate was left still for one hour at room temperature (secondary reaction). After the secondary reaction, the wells were washed with PBS in the same manner, and then 0.8 mM TMB (Tetramethylbenzidine) solution was added thereto at 100 μl per well, to effect color development at 30° C. for five to 20 minutes (color reaction). 100 μl of 1.5 N $H_3PO_4$ was added to each well to stop the color reaction, and the absorbance at 450 nm was measured using a microtiter plate reader. According to the instructions provided by the manufacturer, the measured concentrations were calibrated using a lyophilized control reagent.

Figure 2:
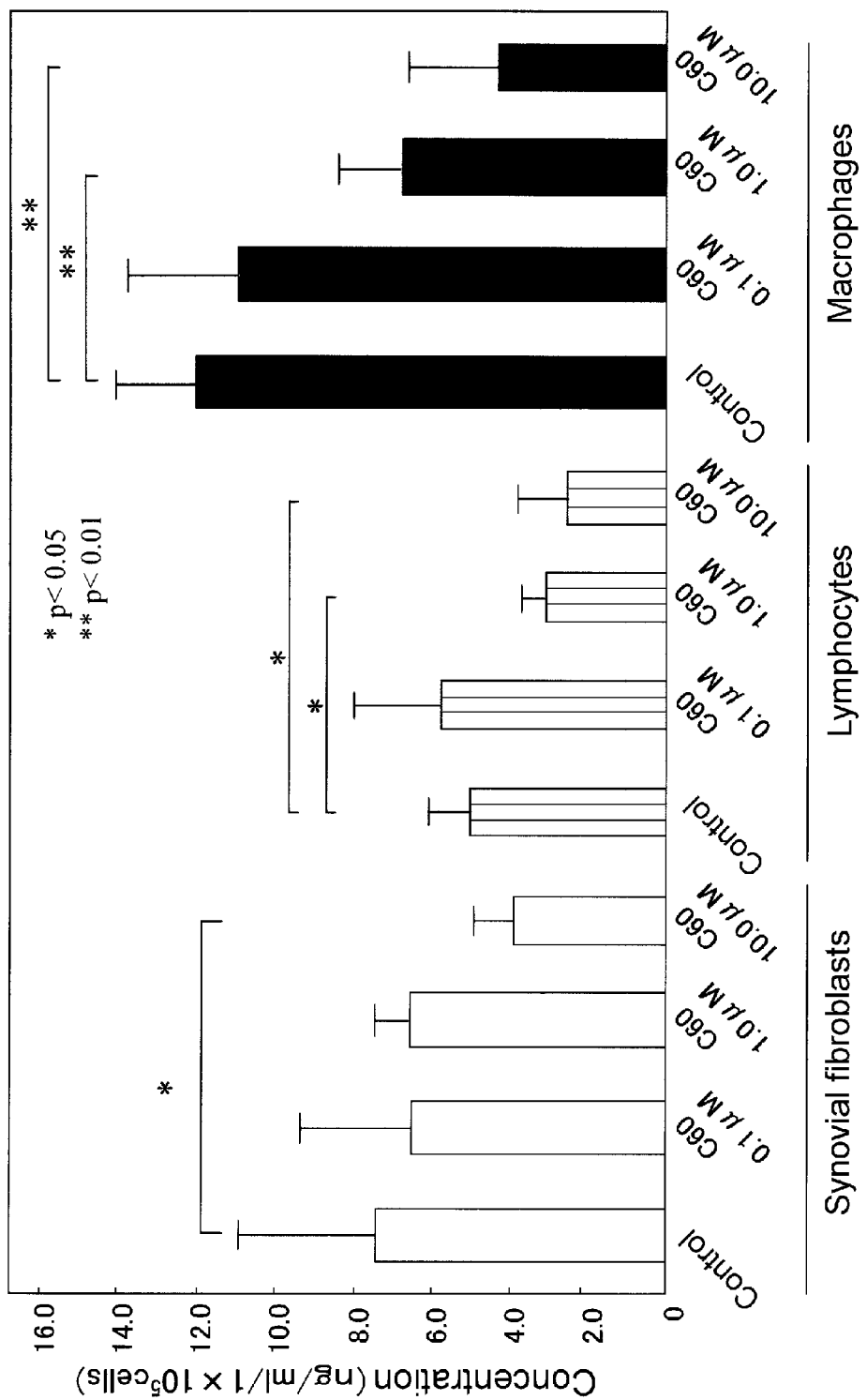
FIG. 2 depicts a graph showing the concentration of TNF-α produced by synovial fibroblasts (n=6), lymphocytes (n=4), and macrophages (n=4) when C60 was added to each type of cells at 0.1, 1.0, and 10.0 μM.
Figure 3:
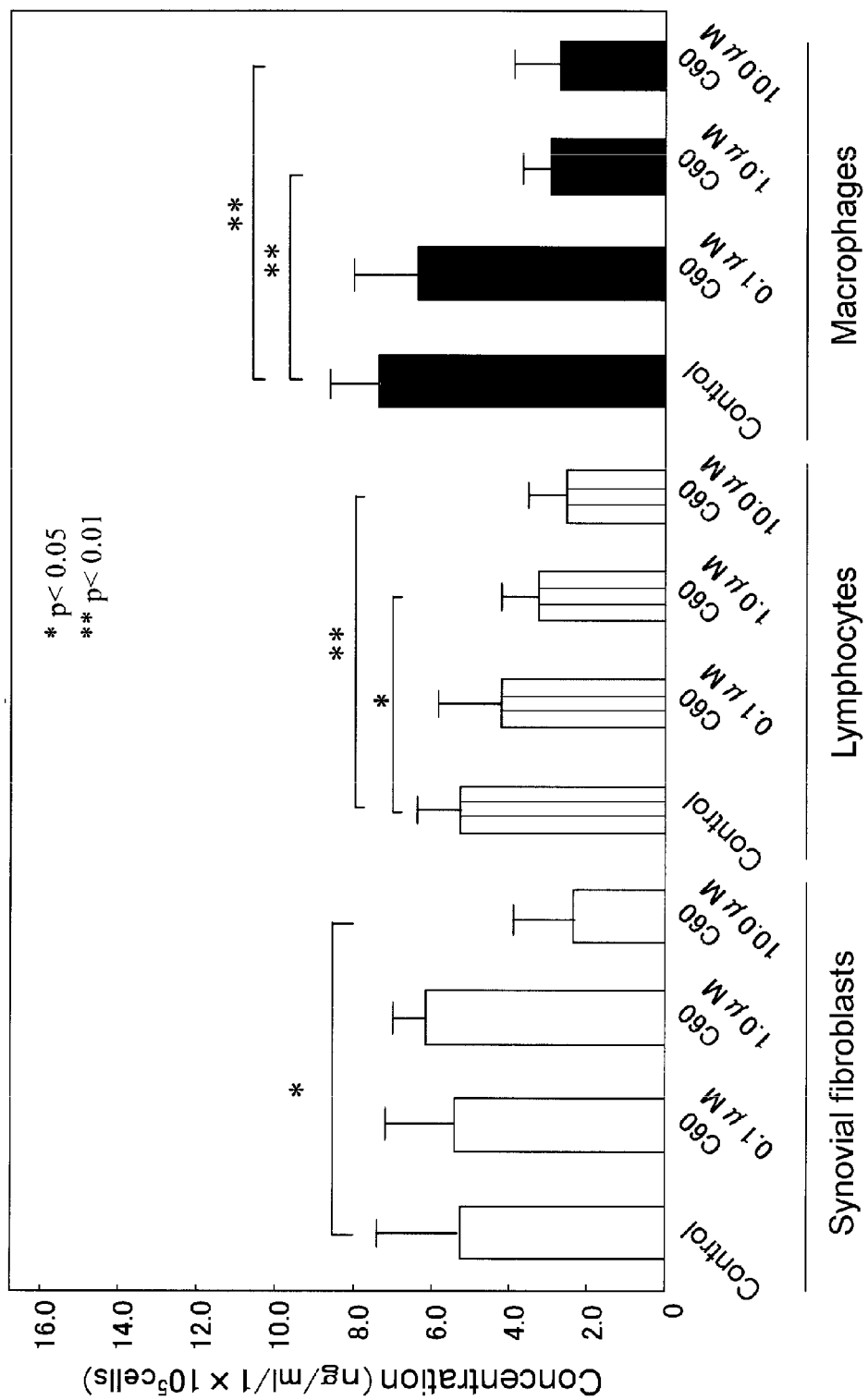
FIG. 3 depicts a graph showing the concentration of IL-1β produced by synovial fibroblasts (n=6), lymphocytes (n=4), and macrophages (n=4) when C60 was added to each type of cell at 0.1, 1.0, and 10.0 μM.

The results are shown in FIGS. 2 and 3. TNF-α and IL-1β concentrations were significantly suppressed in synovial fibroblasts (n=6) with the addition of 10.0 μM C60, and in lymphocytes (n=4) and macrophages (n=4) with the addition of 1.0 μM and 10.0 μM C60, as compared to the control group.

Example 2

Effects of C60 on Bone Destruction and Resorption in Arthritis

In arthritis, particularly rheumatoid arthritis, bone destruction progresses with inflammation. What most impairs daily life with arthritis is the bone destruction associated with synovitis. Differentiation of osteoclasts which participate in bone destruction is induced by inflammation factors, and reactive oxygen is known to be a mediator for this induction. Therefore, whether C60 has an effect of suppressing osteoclast differentiation and bone resorption in arthritis was examined.

Example 2-1

Cell Culture

An osteoclast precursor cell culture kit (Cell Garage Co. Ltd.) was used to observe the effect of C60 on the differentiation of osteoclast precursor cells to mature osteoclasts.

Example 2-2

Effect of C60 on Osteoclast Differentiation

Using the above-mentioned osteoclast precursor cell culture kit, osteoclast precursor cells were cultured on a chamber slide in the presence of osteoclast differentiation-inducing factors. C60 was added to the medium at a final concentration of 0.1, 1.0, or 10.0 μM, and the cells were cultured for seven days. The medium, including various additional factors, was changed to a fresh one every three days. On the seventh day, TRAP-positive multinucleated giant cells, which serve as an index of osteoclast differentiation, were observed by TRAP staining (Cell Garage AK04 Lot: FEM).

The TRAP staining method was carried out as follows. First, after confirming the formation of osteoclasts, the culture solution was removed, and the cells were washed with PBS at 100 μL/well. Next, a fixative solution (kit) was added at 50 μL/well and reacted for five minutes at room temperature. Then, the fixative solution was removed, and the cells were subjected to three washes using 250 μL/well of deionized distilled water (DDW). One vial of chromogenic substrate was dissolved by adding 5 mL of buffer to prepare a color developing solution. The above color developing solution was added at 50 μL/well and then incubated at 37° C. for 20 minutes. After confirming the color development, the color developing solution was removed, and the reaction was stopped using 250 μL/well of DDW. After washing with DDW three times in total, the wells were removed, and the slide was mounted with a water-soluble mounting medium (NUNK 178599 16-well chamber slides were used).

The results are shown in FIG. 4A and FIGS. 5 to 8. Differentiation into mature osteoclasts, in which osteoclast precursor cells turn into TRAP-positive multinucleated giant cells, was significantly suppressed in the presence of 10.0 μM C60.

Example 2-3

Effect of C60 on Bone Resorption by Osteoclasts

Using the above osteoclast precursor cell culture kit, osteoclast precursor cells were cultured on an ivory slice in the presence of osteoclast differentiation-inducing factors. C60 was added to the medium at a final concentration of 0.1, 1.0, or 10.0 μM, and the cells were cultured for 14 days. The medium including various additional factors was changed to a fresh one every three days. On the 14th day, TRAP-positive multinucleated cells, which serve as an index of osteoclast differentiation, were observed by TRAP staining.

The image of bone resorption by osteoclasts was observed by hematoxylin staining of the ivory after removing the osteoclasts seeded thereon. More specifically, a single ivory slice was placed in 1 M aqueous ammonia, sonicated to remove the osteoclasts, and then stained with Mayer's hematoxylin solution for one minute. After the ivory slice was washed with water and dried, the resorption lacunae on the surface of the ivory slice were observed with a phase contrast microscope, and the areas were compared using an image analyzer.

Figure 4:
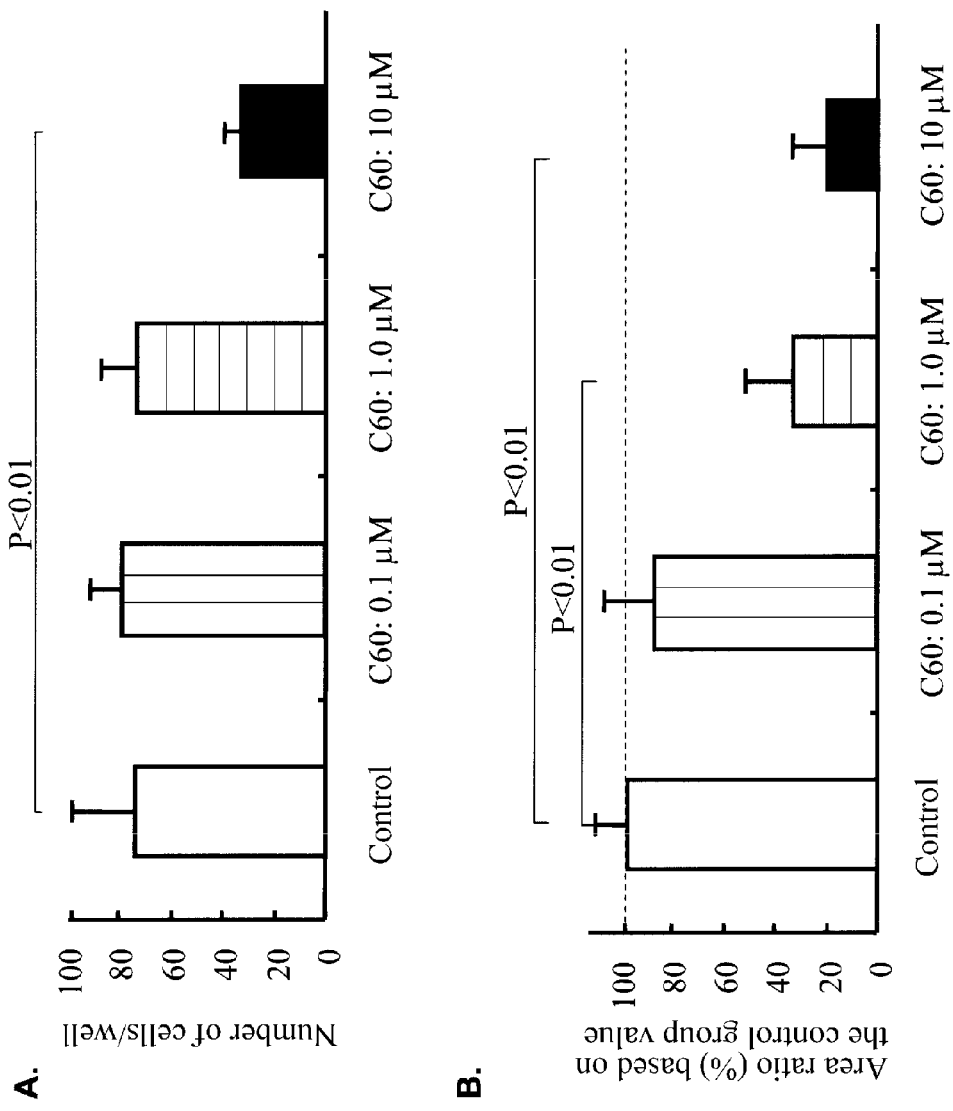
FIG. 4A depicts evaluation of the effect of C60 on osteoclast differentiation.
FIG. 4B depicts a graph in which the bone resorption-suppressing effect of C60 is evaluated.
Figure 5:
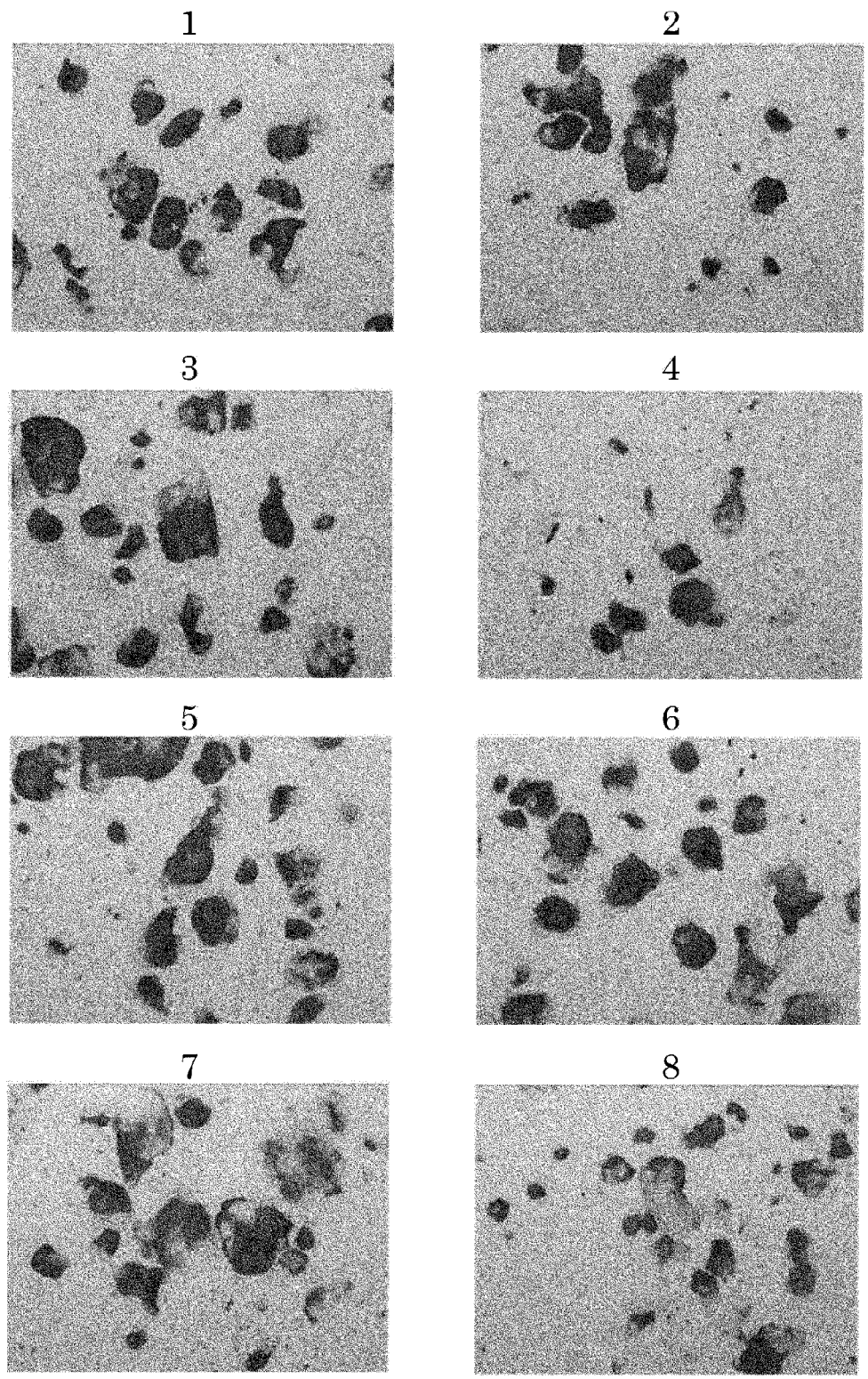
FIG. 5 depicts photographs showing osteoclast differentiation in the absence of C60 observed by TRAP-staining of TRAP-positive multinucleated giant cells.
Figure 6:
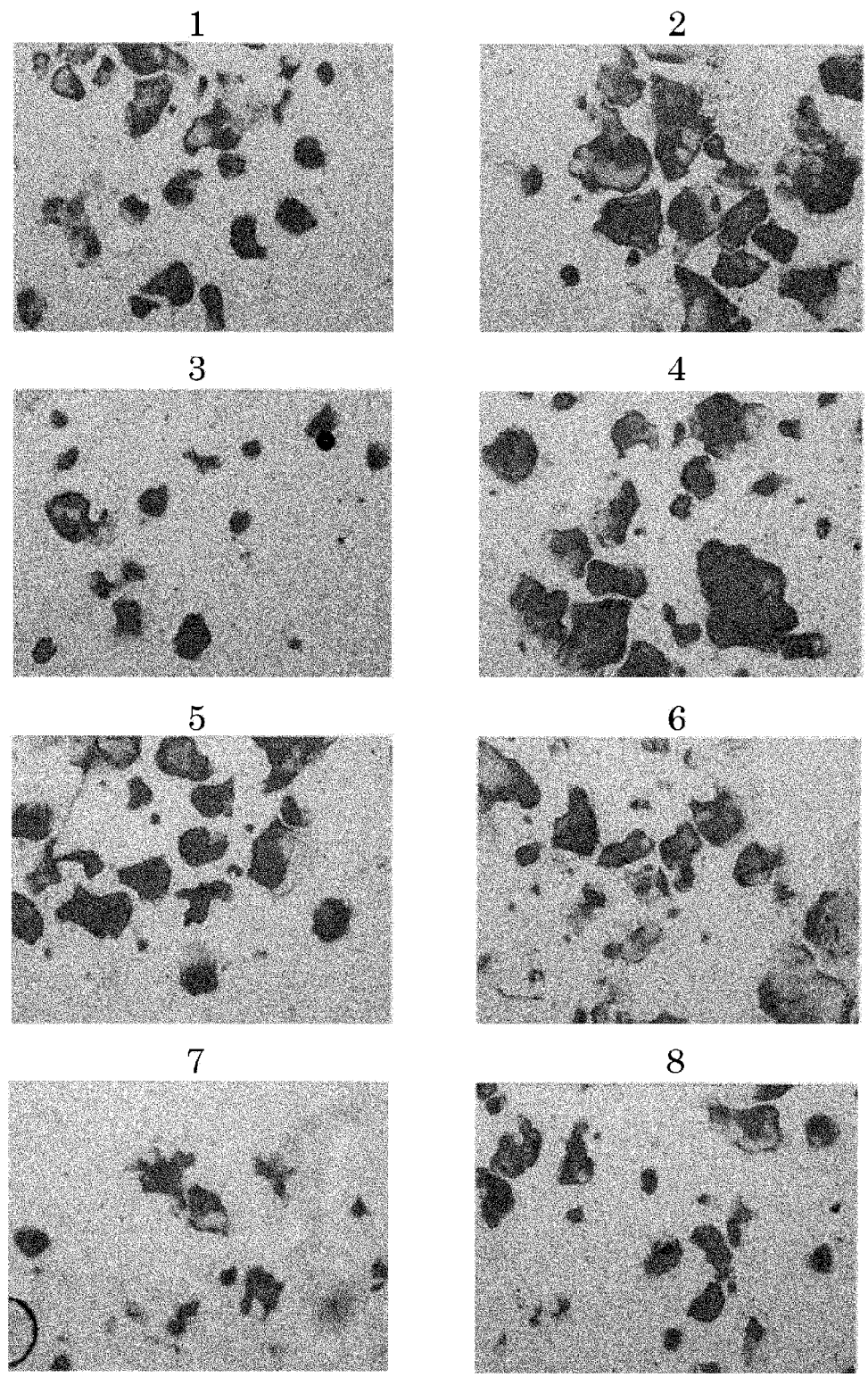
FIG. 6 depicts photographs showing osteoclast differentiation in the presence of 0.1 μM C60 observed by TRAP-staining of TRAP-positive multinucleated giant cells.
Figure 7:
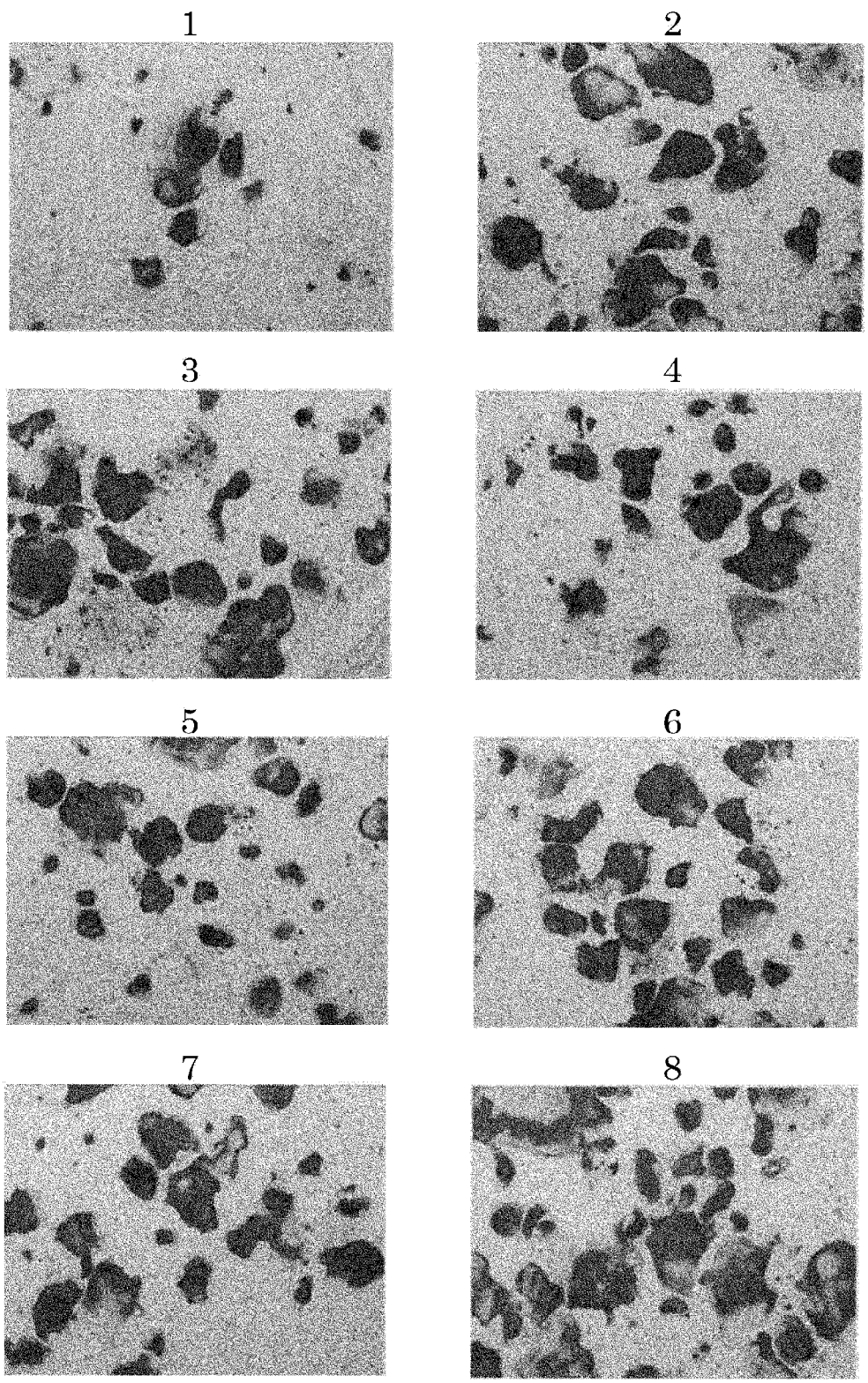
FIG. 7 depicts photographs showing osteoclast differentiation in the presence of 1.0 μM C60 observed by TRAP-staining of TRAP-positive multinucleated giant cells.
Figure 8:
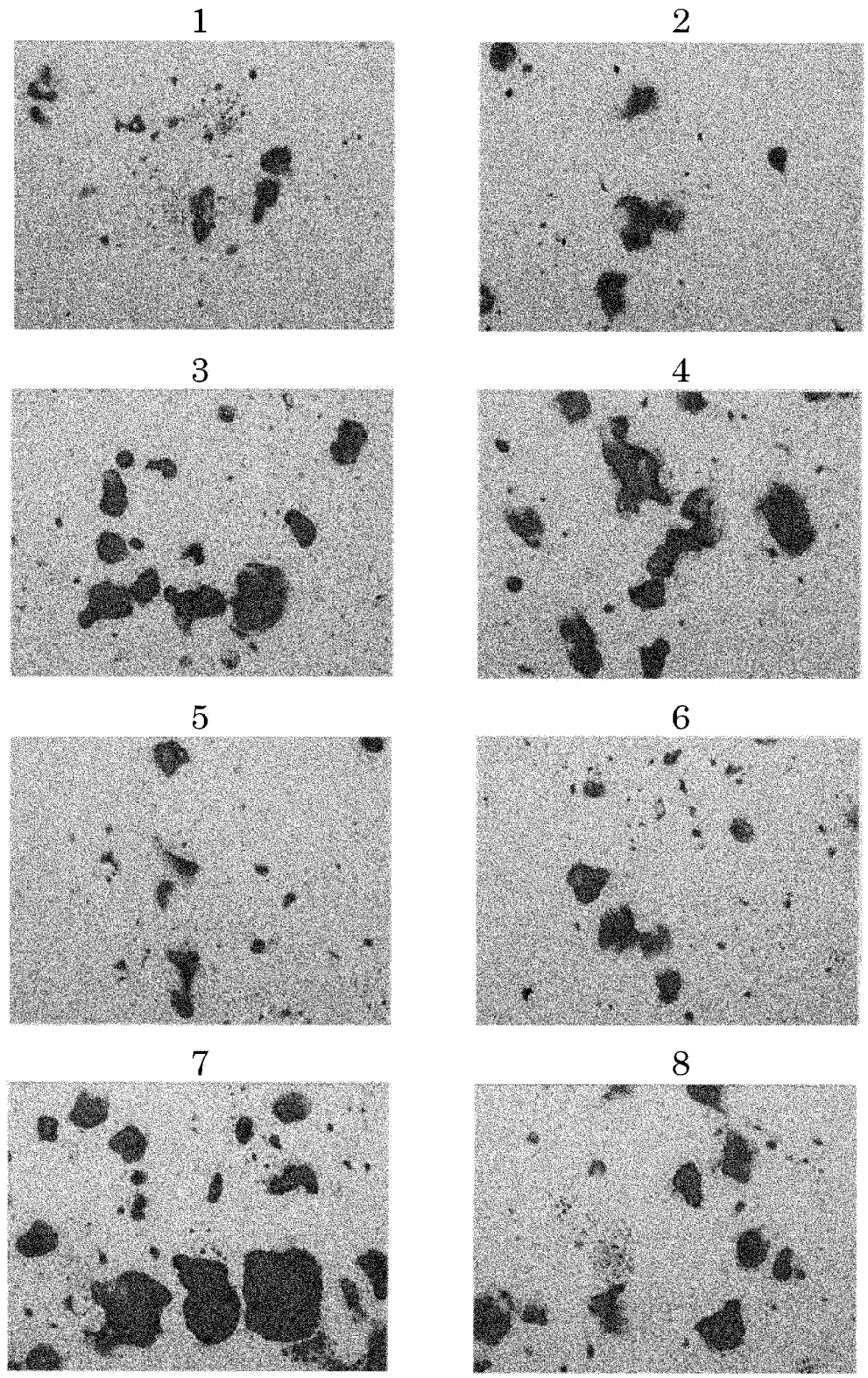
FIG. 8 depicts photographs showing osteoclast differentiation in the presence of 10 μM C60 observed by TRAP-staining of TRAP-positive multinucleated giant cells.
Figure 9:
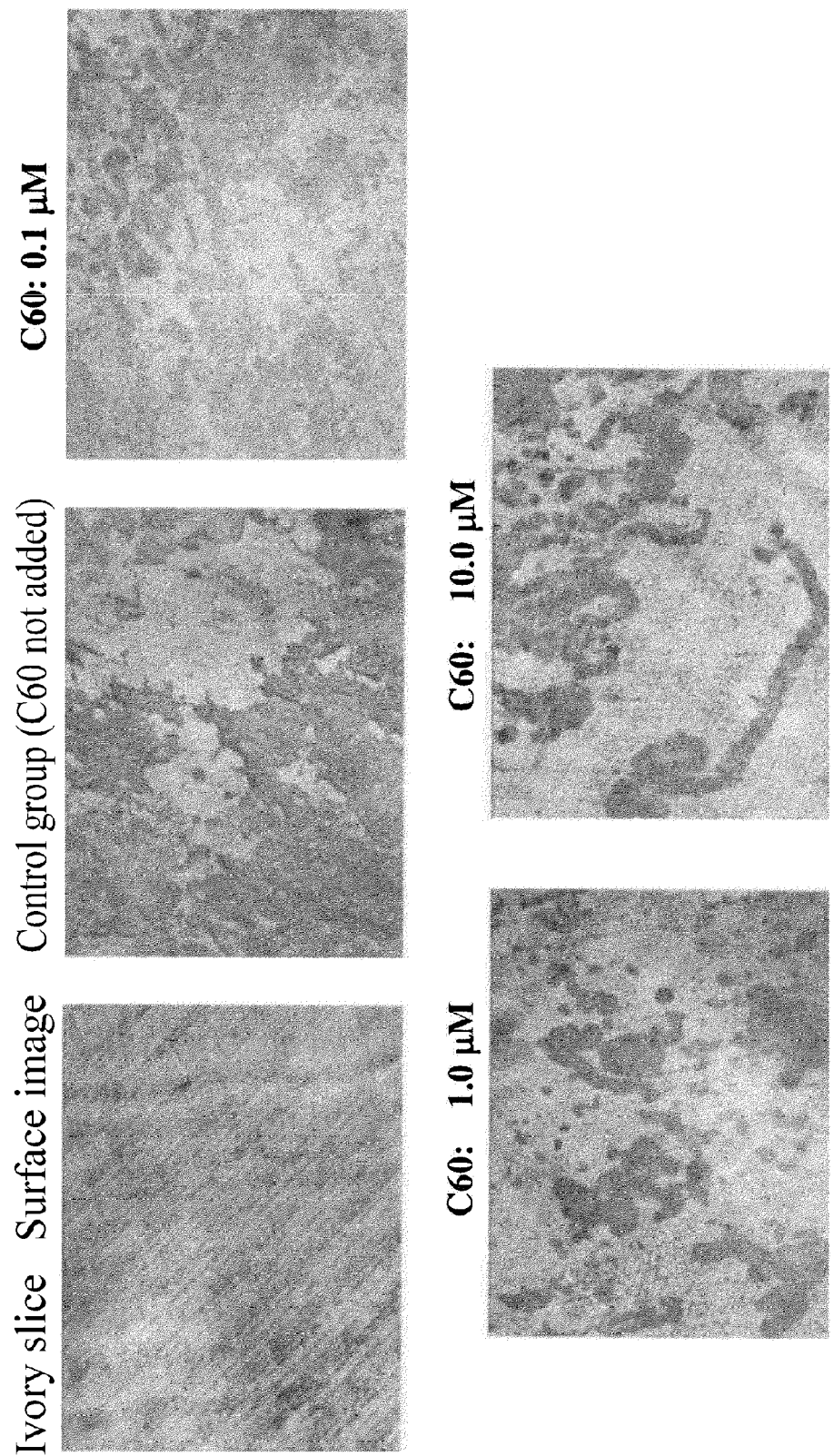
FIG. 9 depicts photographs showing the image of osteoclastic bone resorption observed by hematoxylin staining.

The results are shown in FIG. 4B and FIG. 9. C60 at 1.0 μM or 10.0 μM suppressed the osteoclastic bone resorption.

Example 3

Comparison of C60 with Other Reactive Oxygen Scavengers

Example 3-1

Comparison of Antioxidative Ability Between C60 and Other Reactive Oxygen Scavengers Various concentrations of C60, SOD, and vitamin C solutions were prepared (solvent: DEME medium, SOD (10, and 100 μM), C60 (1, 10, and 100 μM), vitamin C (100 μM)), and the antioxidative ability of each was determined using a kit for measuring antioxidative ability (OXIS Health Product, Oregon, USA) which utilizes the redox reaction of copper.

Figure 10:
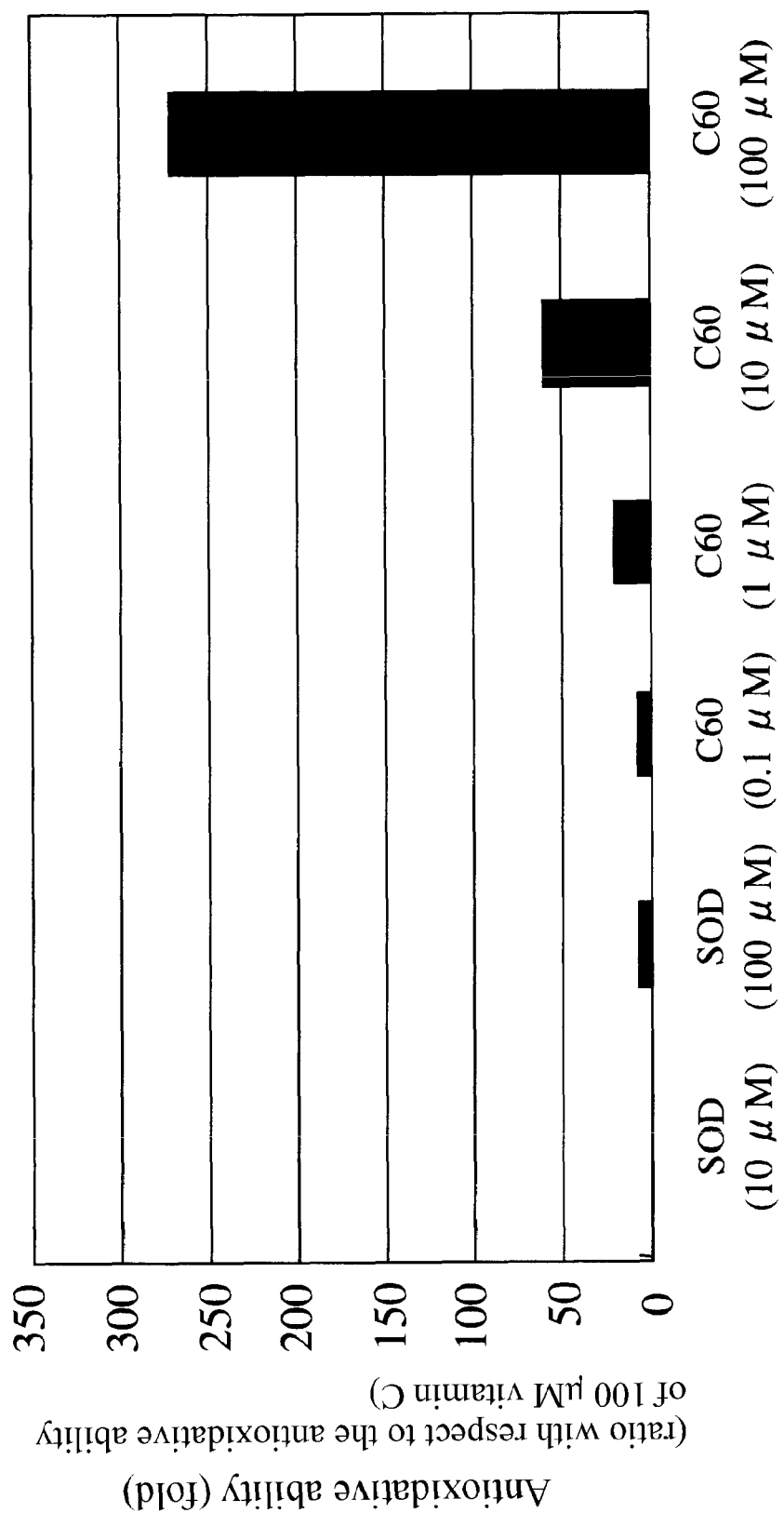
FIG. 10 depicts a graph that compares the antioxidative ability of different reactive oxygen scavengers.

The ratio of each antioxidative ability to that of vitamin C (100 μM) was compared (FIG. 10). The ratio to the antioxidative ability of vitamin C (100 μM) was approximately two-fold for SOD (10 μM), approximately eight-fold for SOD (100 μM), 20-fold for C60 (1 μM), 68-fold for C60 (10 μM), and 270-fold for C60 (100 μM). Comparison at the same concentration of 100 μM shows that while SOD exhibited approximately 8-fold antioxidative ability of vitamin C, C60 had approximately 270-fold antioxidative ability of vitamin C.

Example 3-2

Comparison of the Effect of Suppressing Cytokine Production and the Effect of Suppressing Osteoclast Differentiation Between C60 and Other Reactive Oxygen Scavengers SOD (final concentration: 10 or 100 μM) or vitamin C (final concentration: 10 or 100 μM) was added to DMEM medium. The level of inflammatory cytokines produced by macrophages and the osteoclast differentiation ability were measured by the methods of Examples 1-3 and 2-2 described above, respectively, and compared to the results obtained with C60 (10 μM) (Table 1).

and the C60-administered group, respectively, once a week using a micro-needle syringe. By observing the progress of arthritis over time, arthritis scores (Woods J M. et al., J. Immunology, 166: 1214-1222, 2001) and histopathological scores (Takayanagi H. et al., J. Clinical Investigation, 104: 137-146, 1990) were determined, and the differences between the two groups were statistically compared using Student's t-test. In both groups, the right knee joint was untreated, and comparatively observed for the occurrence and the degree of progress of arthritis.

[4-2] Arthritis Scores

Figure 11:
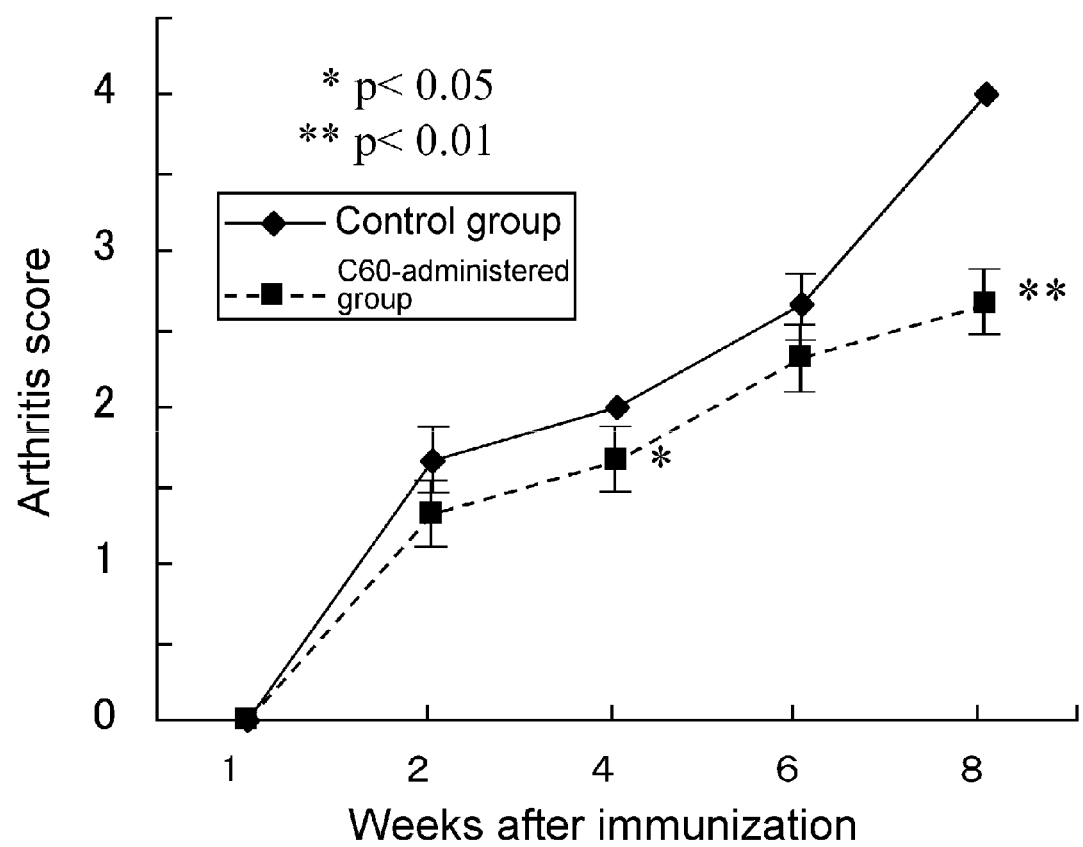
FIG. 11 depicts a graph showing the time course of arthritic score when C60 or a control is administered to the arthritis model. The closed diamonds indicate scores of the control-administered group, and the closed squares indicate scores of the C60-administered group.

Swelling and redness (arthritis scores) of rat knee joints in the control group were found to intensify over time, indicating the induction and aggravation of arthritis. On the other hand, the arthritis scores of the C60-administered group began to show lower values than the average score of the control group from the fourth week after starting the administration, and showed a statistically significant difference in the eighth week. In the sixth week, although the average score was lower in the C60-administered group than in the control group, the individual values varied greatly and showed no significant difference (FIG. 11).

[4-3] Histopathological Scores

Figure 12:
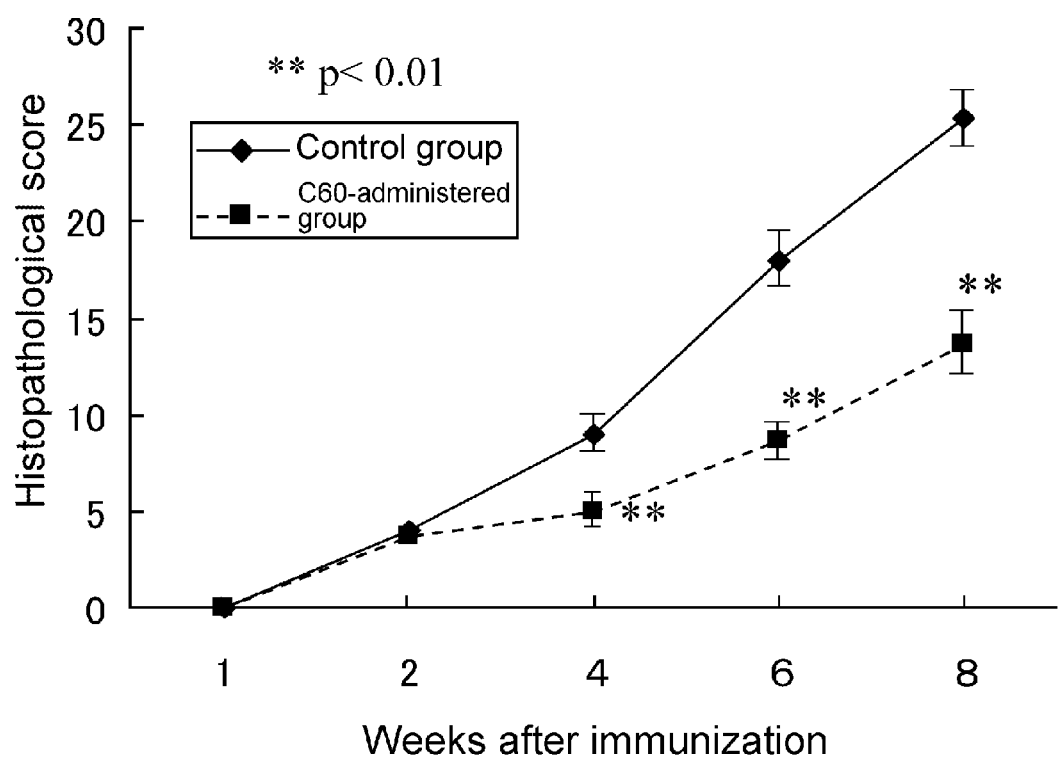
FIG. 12 depicts a graph showing the time course of histopathological score when C60 or a control is administered to the arthritis model. The closed diamonds indicate scores of the control-administered group and the closed squares indicate scores of the C60-administered group.
Figure 13:
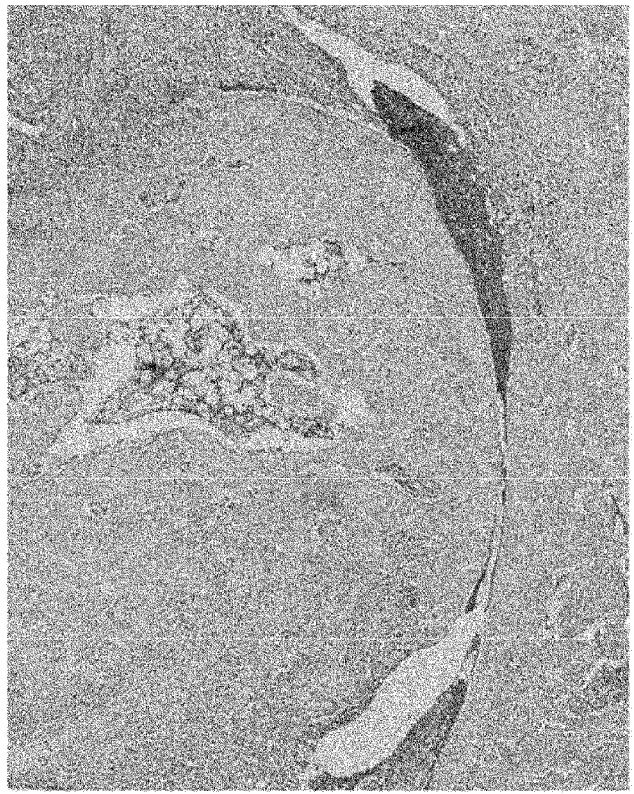
FIG. 13 depicts photographs of articular tissue preparations of the adjuvant arthritis model. The photograph on the left was taken before arthritis induction (before immunization), and the photograph on the right was taken on week four after immunization. In the joint before arthritis induction, the articular cartilage was normal, and synovial membrane proliferation and infiltration of inflammatory cells were not observed. On week four after immunization, the irregularity of articular cartilage surface was observed. The synovial membrane was proliferated and began to invade the bones (osteoclast activation). Infiltration of inflammatory cells was also observed.
Figure 13:
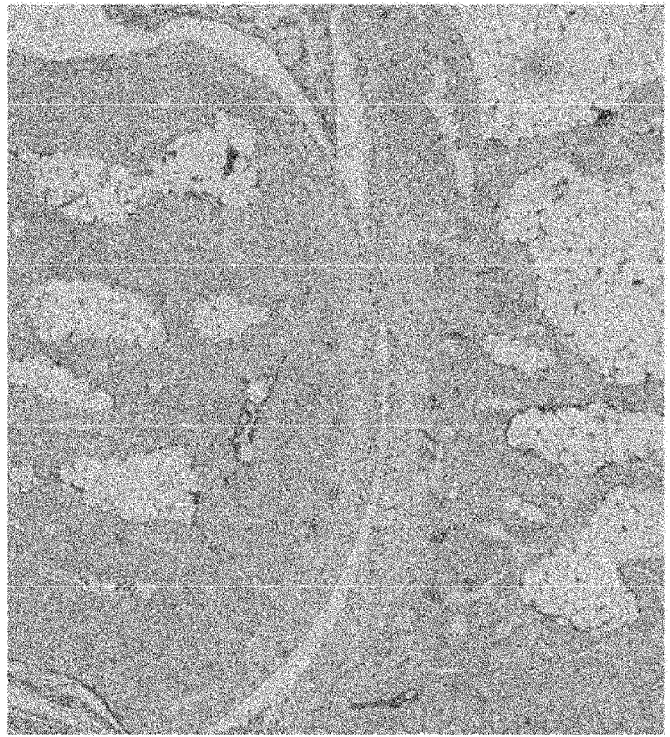
Figure 14:
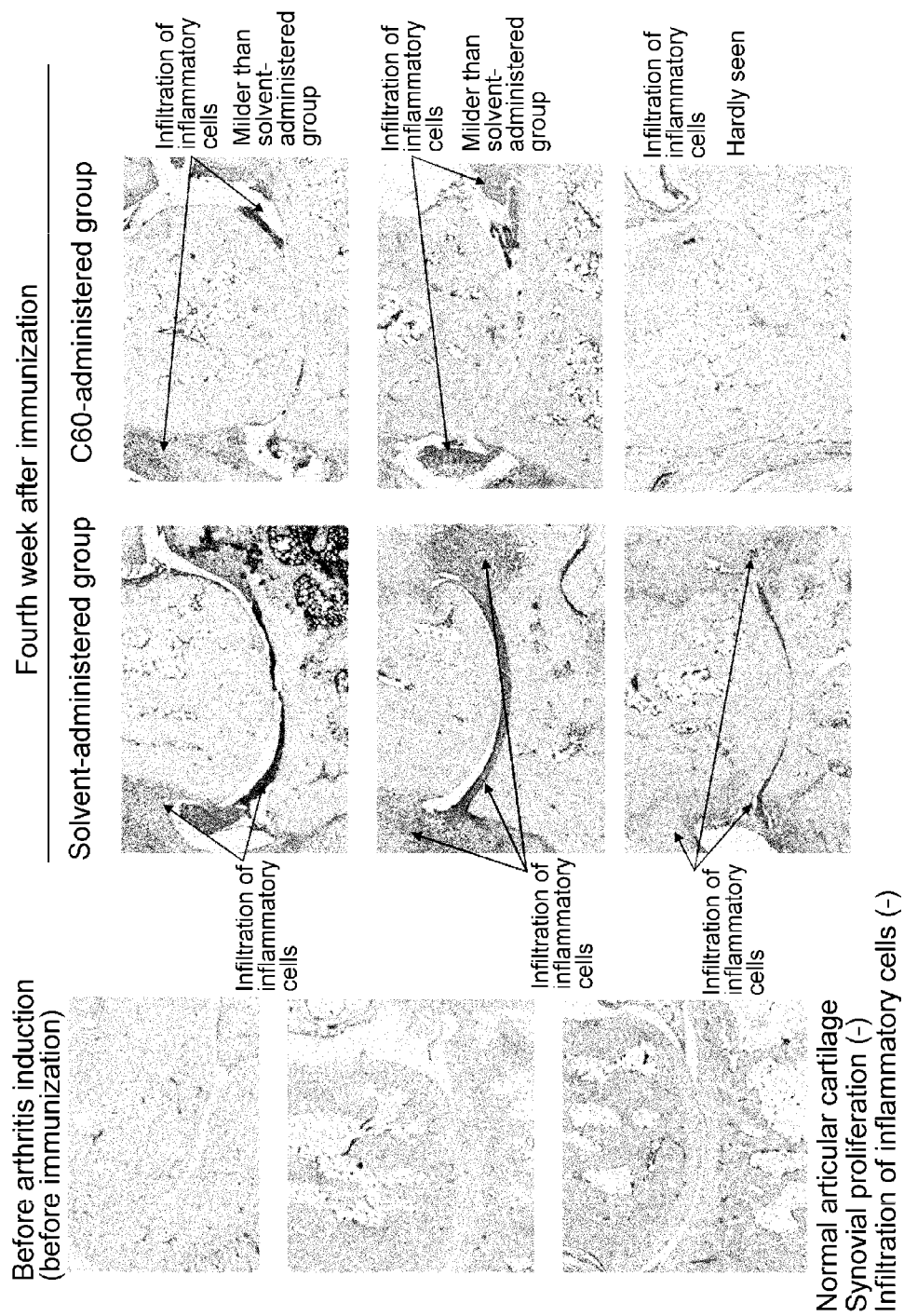
FIG. 14 depicts photographs of articular tissue preparations of the adjuvant arthritis model (before arthritis induction and on the fourth week after immunization). Before arthritis induction, all three animals showed normal articular cartilage, no synovial membrane proliferation, and no inflammatory cell infiltration. On the fourth week after immunization, inflammatory cell infiltration was observed in all animals of the control group (solvent-administered group). On the other hand, the C60-administered group showed almost no or milder inflammatory cell infiltration than the control group.
Figure 15:
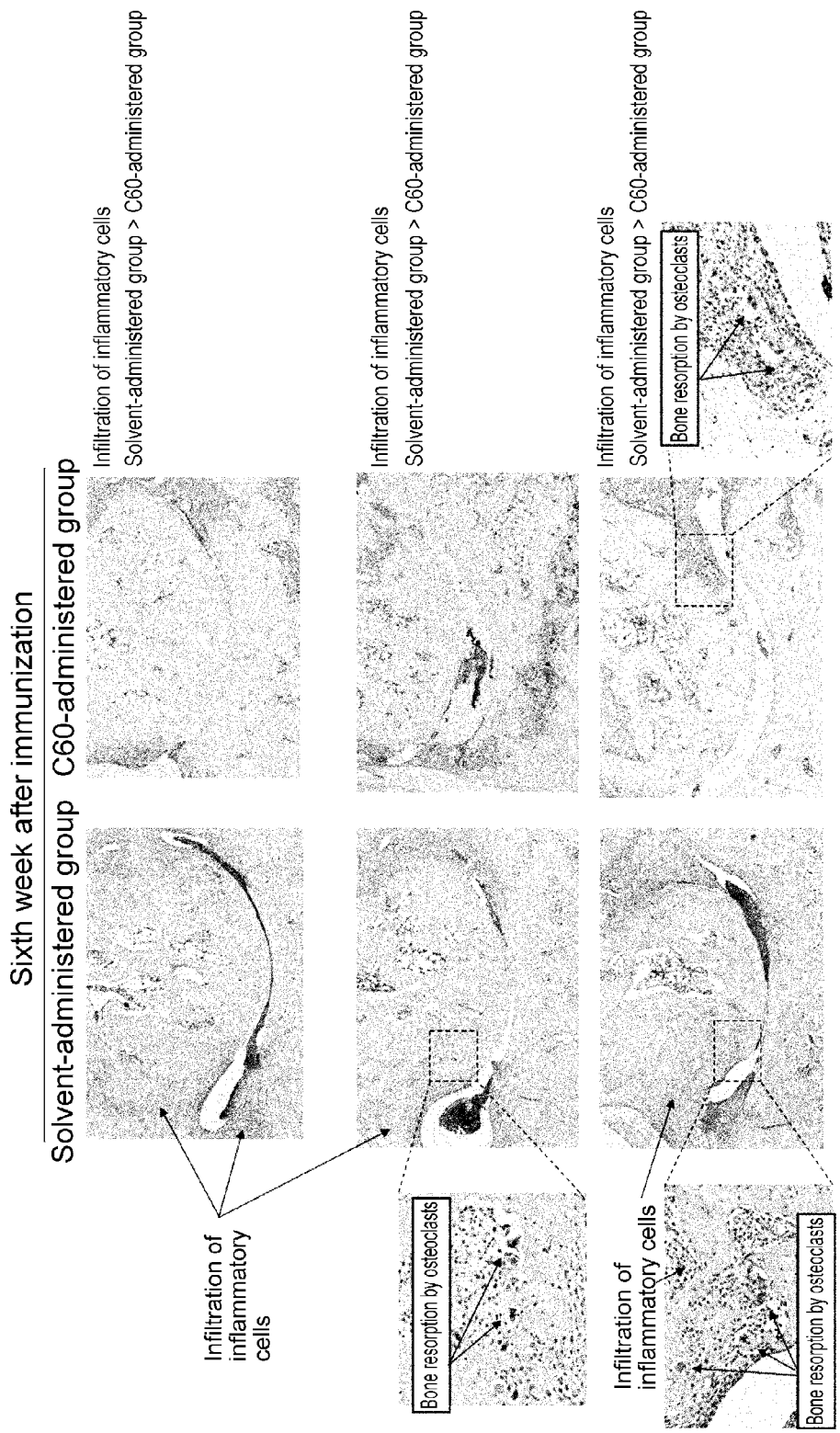
FIG. 15 depicts photographs of articular tissue preparations of the adjuvant arthritis model (on the sixth week after immunization). Infiltration of inflammatory cells was observed in all three animals of the control group (left column). Two animals also showed osteoclastic bone resorption (middle and bottom panels of the left column). While infiltration of inflammatory cells was also observed in the three animals of the C60-administered group (right column), it is milder than the control group.
Figure 16:
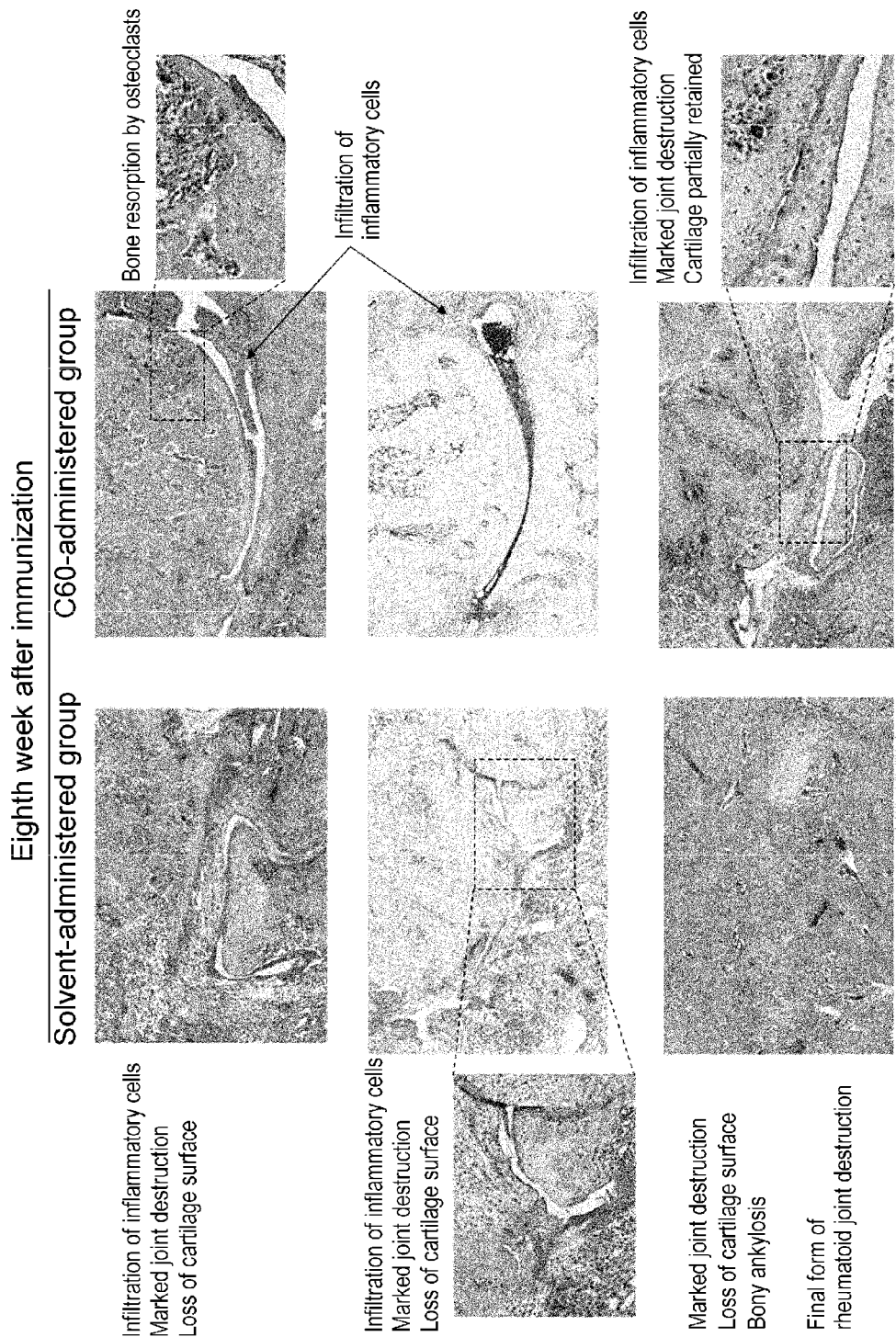
FIG. 16 depicts photographs of articular tissue preparations of the adjuvant arthritis model (on the eighth week after immunization). Two animals of the control group showed inflammatory cell infiltration, marked articular destruction, and disappearance of cartilage surface (top and middle panels of the left column). One animal showed bony ankylosis as well as marked articular destruction and disappearance of cartilage surface, indicating the final form of rheumatoid joint destruction (bottom panel of the left column). On the other hand, in the C60-administered group, while marked articular destruction was observed in one animal, a part of the cartilage was intact (bottom panel of the right column).

Histopathological changes also showed a tendency similar to those of the swelling and redness of the joints (arthritis scores). Specifically, arthritis and osteochondral destruction progressed over time in both groups, but the histopathological scores of the C60-administered group were statistically significantly lower than those of the control group from the fourth week after starting the administration (FIG. 12). Photographs of the histopathological preparations are shown in FIGS. 13 to 16.

TABLE 1

| | Concentration of added antioxidant (μM) | Concentration of cytokines produced by macrophage (ng/ml/1 × $10^5$ cells) | | Osteoclast differentiation (TRAP-positive multinucleated giant cells/well) |
|---|---|---|---|---|
| | | TNF - α | IL - 1β | |
| Medium only | — | 122 | 8.1 | 78 |
| C60 | 10 | 55 * | 3.4 * | 37 * |
| SOD | 10 | 130 | 9.0 | 82 |
| | 100 | 106 | 7.8 | 75 |
| Vitamin C | 10 | 116 | 6.9 | 94 |
| | 100 | 115 | 7.5 | 82 |

* $P < 0.01$, SOD: Superoxide dismutase

When compared to the control (medium alone), only C60 showed significant suppressive effects against the cytokine (TNF-α and IL-1β) production by macrophages and the osteoclast differentiation.

Example 4

Effects of C60 on Arthritis Model

The results of Examples 1 and 2 using cultured cells suggested that C60 has the potential to suppress inflammation and bone resorption/destruction. Therefore, suppressive effects of C60 on arthritis (inflammation and osteoarticular destruction) were examined using an animal model for arthritic diseases.

[4-1] Methods

Adjuvant arthritis rats were prepared according to a known report (Yamamoto A. et al., Arthritis & Rheumatism, 48: 2682-2692, 2003). After the first immunization for arthritis induction, the rats were divided into two groups. 20.0 μL of phosphate buffered saline (PBS) and 20.0 μL of C60 (10.0 μM) were injected into the left knee joint of the control group

INDUSTRIAL APPLICABILITY

The present invention provides novel pharmaceutical agents effective for diseases associated with arthritis, including rheumatoid arthritis. The present pharmaceutical agents can provide new therapeutic options to patients for whom conventional anti-rheumatic agents are not effective, and to patients who have limitations when it comes to available pharmaceutical agents due to complications and such.

The invention claimed is:

1. A method for treating arthritis or bone destruction associated with arthritis in a patient, comprising the step of administering to the patient at least one selected from the group consisting of an un-substituted fullerene, a clathrate fullerene, and a fullerene derivative, wherein the fullerene derivative is selected from the group consisting of heterofullerene, norfullerene, homofullerene, secofullerene, a fullerene polymer, a fullerene substituted with a hydroxyl group, an amino group, or a carboxyl group and salts thereof, wherein a dosage is 0.1 μM to 100 μM per affected part, thereby treating the arthritis or bone destruction associated with arthritis in the patient.

2. The method of claim 1, wherein the arthritis is associated with rheumatoid arthritis, rheumatoid arthritis-related disease, autoimmune disease, or osteoporosis.

3. The method of claim 2, wherein the rheumatoid arthritis-related disease is at least one selected from the group consisting of malignant rheumatoid arthritis, Felty's syndrome, and Caplan's syndrome.

4. The method of claim 2, wherein the autoimmune disease is at least one selected from the group consisting of systemic lupus erythematosus, polymyositis, psoriatic arthritis, Behcet's disease, Sjogren's syndrome, mixed connective tissue disease, and overlap syndrome.

5. The method of any one of claims 1, 2, 3, and 4, wherein the fullerene is C60.

6. The method of claim 2, wherein the arthritis is associated with rheumatoid arthritis.

* * * * *

UNITED STATES PATENT AND TRADEMARK OFFICE
CERTIFICATE OF CORRECTION

| | | |
|---|---|---|
| PATENT NO. | : 8,440,893 B2 | |
| APPLICATION NO. | : 12/445858 | |
| DATED | : May 14, 2013 | |
| INVENTOR(S) | : Kazuo Yudoh | |

It is certified that error appears in the above-identified patent and that said Letters Patent is hereby corrected as shown below:

On the Title Page:

In the Assignee section, item (73), page 1, first column, line 3, please replace "Corporaion" with --Corporation--.

Signed and Sealed this
Twenty-fourth Day of September, 2013

Teresa Stanek Rea
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,440,893 B2 | Page 1 of 1 |
| APPLICATION NO. | : 12/445858 | |
| DATED | : May 14, 2013 | |
| INVENTOR(S) | : Yudoh | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 536 days.

Signed and Sealed this
Sixth Day of January, 2015

Michelle K. Lee
*Deputy Director of the United States Patent and Trademark Office*